(12) United States Patent
Nguyen et al.

(10) Patent No.: US 11,185,273 B2
(45) Date of Patent: Nov. 30, 2021

(54) DEVICE, SYSTEM AND USE OF A CATHETER SYSTEM TO RECORD AND MAP CARDIAC RHYTHM

(71) Applicant: BIOSENSE WEBSTER (ISRAEL) LTD., Yokneam (IL)

(72) Inventors: Don K. Nguyen, Anaheim, CA (US); Qun Sha, Diamond Bar, CA (US); Zhong (Jack) Wang, San Marino, CA (US); Jamie Lynn Malinaric, Pasadena, CA (US); Dustin R. Tobey, San Dimas, CA (US); Shubhayu Basu, Anaheim, CA (US); Cesar Fuentes-Ortega, Pasadena, CA (US); Pieter Emmelius Van Niekerk, Monrovia, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 16/912,567

(22) Filed: Jun. 25, 2020

(65) Prior Publication Data
US 2020/0323456 A1 Oct. 15, 2020

Related U.S. Application Data

(63) Continuation of application No. 16/781,952, filed on Feb. 4, 2020.
(Continued)

(51) Int. Cl.
*A61B 5/287* (2021.01)
*A61B 5/00* (2006.01)
*A61B 5/361* (2021.01)

(52) U.S. Cl.
CPC .............. *A61B 5/287* (2021.01); *A61B 5/361* (2021.01); *A61B 5/6859* (2013.01)

(58) Field of Classification Search
CPC ....... A61B 5/042; A61B 5/0422; A61B 5/046; A61B 5/6852; A61B 5/6859; A61B 18/1492; A61B 1/06; A61N 2001/0585
See application file for complete search history.

(56) References Cited

U.S. PATENT DOCUMENTS 6,236,883 B1 * 5/2001 Ciaccio .................. A61B 5/363
600/515
7,089,045 B2 8/2006 Fuimanono et al.
(Continued)

OTHER PUBLICATIONS

Frontera, A. et al. Electrogram signature of specific activation patterns: Analysis of atrial tachycardias at high-density endocardial mapping (2017). Heart Rhythm, vol. 15, No. 1, pp. 28-37 (Year: 2018).*

*Primary Examiner* — Eun Hwa Kim
(74) *Attorney, Agent, or Firm* — Troutman Pepper Hamilton Sanders LLP

(57) ABSTRACT

A catheter system to record and map electrical signals by cardiac tissues before, during, and/or after the treatment of cardiac arrhythmias in a group of patients. The system can include an elongated body; a distal electrode assembly comprising a proximal stem, a plurality of spines emanating from the stem; and a plurality of nonconductive spine covers, each surrounding a respective spine. Each spine can cover one or more tensile members of the respective spine cover. The system can be configured to achieve clinically improved performance and safety of catheter configurations as to accessibility into target areas of a beating heart.

13 Claims, 46 Drawing Sheets

Related U.S. Application Data

(60) Provisional application No. 62/815,227, filed on Mar. 7, 2019.

(56) References Cited

U.S. PATENT DOCUMENTS

| | | |
|---|---|---|
| 7,155,270 B2 | 12/2006 | Solis et al. |
| 7,228,164 B2 | 6/2007 | Fuimaono et al. |
| 7,302,285 B2 | 11/2007 | Fuimaono et al. |
| 2009/0005773 A1 | 1/2009 | Beeckler et al. |
| 2016/0228023 A1* | 8/2016 | Govari .................. A61B 5/7203 |
| 2018/0296111 A1* | 10/2018 | Deno ...................... A61B 5/746 |
| 2019/0239765 A1 | 8/2019 | Fuentes-Ortega et al. |
| 2019/0239766 A1 | 8/2019 | Fuentes-Ortega et al. |
| 2019/0239810 A1 | 8/2019 | Solis et al. |
| 2019/0239812 A1 | 8/2019 | Botzer et al. |
| 2019/0357793 A1* | 11/2019 | Ruppersberg .......... A61B 34/20 |

\* cited by examiner

| Catheter | Physical Description | | | | | |
|---|---|---|---|---|---|---|
| | Spine Length (mm) | Shaft Diameter Size (FR) | Curve Type | Electrode Spacing | Coverage Area (cm$^2$) | Count |
| Catheter A | 15 | 7.5 | D | 2-2-2-2-2 | 7.1 | 48 |
| Catheter B | 20 | 7.5 | D | 2-5-2-5-2 | 12.6 | 48 |
| Catheter C | 20 | 7.5 | D | 3-3-3-3-3 | 12.6 | 48 |

Fig. 6A

| Catheter | Physical Description | | | | | |
|---|---|---|---|---|---|---|
| | Spine Length (mm) | Bipolar Channels | Unipolar Channels | Electrode Spacing | Size (μm) | Density (electrode/cm$^2$) |
| Catheter A | 15 | 40 | 8 | 2-2-2-2-2 | 800 | 7 |
| Catheter B | 20 | 40 | 8 | 2-5-2-5-2 | 460 | 4 |
| Catheter C | 20 | 0 | 48 | 3-3-3-3-3 | 460 | 4 |

Fig. 6B

| Investigational Devices | Function |
|---|---|
| Mapping Catheter | Recording and mapping of cardiac chambers with the system throughout the study procedure. |
| Non-investigational Devices/ Standard Equipment | Function |
| 8.5 F compatible sheath. | Facilitate deployment of catheter into the cardiac chambers |
| EP lab recording equipment | Records multiple intracardiac electrograms and signals from the RF generator (power, temperature, impedance) and performs electrical stimulation. |
| Visualization System | For mapping and visualization information. |
| User Interface Junction Box | Provide the interface to the catheter, generator, and the Visualization System. |

Fig. 8

Using Catheter Catheter in place of the institution's standard diagnostic catheter choice (e.g. LASSO® Catheter or PENTARAY® Catheter) for the study qualifying arrhythmia. Any use of a non-investigational mapping catheter in place of the OCTARAY™ will result in a failure of the primary study endpoint.

The CARTO 3 system will be used to "bookmark" instances of:
- abnormal study catheter "noise"
- arrhythmias initiated by study catheter manipulation (e.g. PVCs)
- focal activation patterns or rotational activation patterns identified (only for 4D LAT mapping).

Pre-Ablation Mapping with OCTARAY™ catheter
Pre-ablation mapping for AT, re-do PAF or VT is considered complete when ALL of the following are accomplished, as applicable:
1. the entire chamber and areas associated with the targeted arrhythmia(s) are completely mapped using fast anatomical mapping (FAM)
2. Substrate or previous lesion line associated with the arrhythmia(s) is mapped
    a. Local activation mapping required for complex AT and VT procedures
    b. Voltage mapping required for re-do PAF and VT procedures
3. Conduction channel, gap(s) and critical isthmus are identified (as applicable)
4. Mapping density at the areas of interests (e.g. slow conduction zones) is adequate (target data interpolation between points ≤5mm)

Local activation mapping is required to be performed for complex AT and VT mapping. Voltage mapping is required to be used in pre-ablation mapping for re-do PAF and VT procedures.

PsAF pre-ablation mapping is considered complete when the atrium is completely mapped using the FAM algorithm AND the 4D LAT algorithm is used to map the entire left atrium (and right atrium, if applicable) using the CARTO® 3 System's CARTOFINDER™ Module. The OCTARAY™ catheter should be placed to maximize contact with the endocardium and 30-second 4D LAT recordings will be taken in succession until the entire atrium is mapped.

Standard of Care Ablation Procedure
Treatment of study arrhythmias will be per institution's standard of care (SOC).

Post-SOC Ablation Mapping with OCTARAY™ catheter
If additional mapping is clinically indicated, the OCTARAY™ catheter is required to be used.

Fig. 9

| Assessments | Screening / Baseline (Clinic Visit) | Study Procedure | Discharge | 7-day Follow-up (Clinic Visit or Phone call) |
|---|---|---|---|---|
| Informed Consent | ✓ | | | |
| Demographics | ✓ | | | |
| Medical and Cardiac History | ✓ | | | |
| Transthoracic Echo (TTE) | ✓ | | | |
| Pregnancy Test | ✓ | | | |
| Thrombus detection | | ✓ | | |
| Adverse Events | ✓ | ✓ | ✓ | ✓ |

Fig. 10

| | |
|---|---|
| Mild | Awareness of signs, symptoms, or events that are otherwise easily tolerated that may result in minimal transient impairment of a body function or damage to a body structure, but do not require intervention other than monitoring. |
| Moderate | Any event that results in moderate transient impairment of a body function or damage to a body structure that causes interference with usual activities, or that warrants possible intervention, such as the administration of medication, to prevent permanent impairment of a body function or damage to a body structure. |
| Severe | Any event that is incapacitating (an inability to do usual activities) or is life-threatening and results in permanent impairment of a body function or damage to a body structure, or requires intervention, such as major surgery, to prevent permanent impairment of a body function or damage to a body structure. |

Fig. 11

| Caused By | Relation | Definition of Relation |
|---|---|---|
| Device | Definitely (causal relationship) | The event is associated with the investigational device beyond reasonable doubt |
| | Probable | The relationship with the use of the investigational device seems relevant and/or the event cannot be reasonably explained by another cause, but additional information may be obtained |
| | Possibly | The relationship with the use of the investigational device is weak but cannot be ruled out completely |
| | Unlikely | The relationship with the use of the investigational device seems not relevant and/or the event can be reasonably explained by another cause, but additional information may be obtained |
| | Not related | Relationship to the investigational device can be excluded |
| Study Procedure | Definitely (causal relationship) | The event is associated with the study procedure beyond reasonable doubt |
| | Probable | The relationship with the study procedure seems relevant and/or the event cannot be reasonably explained by another cause, but additional information may be obtained |
| | Possibly | The relationship with the study procedure is weak but cannot be ruled out completely |
| | Unlikely | The relationship to the study procedure seems not relevant and/or the event can be reasonably explained by another cause, but additional information may be obtained |
| | Not related | Relationship to the procedure can be excluded |

Fig. 12

| Classification | | Definition |
|---|---|---|
| Resolved without sequelae | | Subject fully recovered with no observable residual effects |
| Resolved with sequelae | | Subject recovered with observable residual effects |
| Ongoing | Improved | Subject's condition improved, but residual effects remain |
| | Unchanged | AE is ongoing without changes in the overall condition |
| | Worsened | Subject's overall condition worsened |
| Death | | Subject died as a result of the AE (whether or not the AE is related to the device or procedure) |

Fig. 13

| Anticipated Adverse Events ||
|---|---|
| Acute Respiratory Distress Syndrome (ARDS) | Diaphragmatic paralysis |
| Air embolism | Dislodgement of permanent pacing leads |
| Allergic reaction | Disseminated Intravascular Coagulation |
| Allergic reaction to Anesthesia (e.g., hair loss) | Dyspnea |
| Anaphylactic shock | Endocarditis |
| Anemia | Epistaxis |
| Anesthesia reaction | Expressive aphasia |
| Apnea - sedation induced | Fainting |
| Arrhythmia: bradycardia (not pre-existing) | Fatigue |
| Arrhythmia: pro-arrhythmias (not pre-existing) | Gastric reflux |
| Arrhythmia: tachycardia (not pre-existing) | Gastrointestinal diverticulosis |
| Asthmatic attack | Gastro-intestinal NOS |
| Atelectasis | Heart Failure |
| Atrial fibrillation (not pre-existing) | Hematoma (local) /ecchymosis |
| Atrio-Esophageal fistula | Hemorrhage |
| Atypical left atrial flutter (not pre-existing) | Hemothorax |
| AV fistula | High / increased creatine phosphokinase (CPK) |
| Bleeding complications | Hypotension |
| Bleeding requiring transfusion | Hypoxia |
| Cardiac arrest | Increase in frequency or duration of episodes of typical atrial flutter |
| Cardiac perforation | |
| Cardiac thrombo-embolism | Increased phosphokinase level |
| Cerebro-vascular accident (CVA) / stroke | Infection, localized |
| Chest pain/discomfort | Infection, systemic |
| Complete heart block, temporary or permanent | Injury to skin, muscle, connective tissue due to body position, electrical cardioversion, etc. |
| Conduction block: ongoing / resolved | |
| Congestive Heart Failure | Laceration |
| Coronary artery dissection | Leakage of air or blood into the lungs or other organs due to perforation |
| Coronary artery occlusion | |
| Coronary artery spasm | |
| Coronary artery Thrombosis | |
| Damage to the vascular system | |
| Death | |
| Deep venous thrombosis | |

Fig. 14

| Anticipated Adverse Events ||
|---|---|
| Liver toxicity | Respiratory depression |
| Local hematoma/ecchymosis | Respiratory failure |
| Mobile strands in Inferior Vena Cava | Retroperitoneal hematoma |
| Myocardial Infarction | Rhabdomyolysis, including produced by body position or propofol |
| Nausea | |
| Neurological disorders (headache) | Sedation induced CO2 retention with lethargy and cholecystitis |
| Neurological disorders (poor coordination) | |
| Neurological disorders (tremor) | Seizure |
| Obstruction to the vascular system | Sepsis |
| Palpitations | Skin burns (due to cardioversion, tape, etc) |
| Perforation to the vascular system | Skin discoloration |
| Pericardial effusion resulting in tamponade | Skin injury / muscle or connective tissue injury due to body position, electrical cardioversion |
| Pericardial effusion without tamponade | |
| Pericarditis | |
| Peripheral embolus | Skin rash |
| Peripheral nerve injury | Tamponade |
| Peripheral thromboembolism | Temperature elevation |
| Phlebitis | Thrombocytopenia |
| Phrenic nerve damage | Thromboembolism |
| Pleural effusion | Thrombosis |
| (Aspiration) pneumonia | Thyroid disorders |
| Pneumothorax | Transient extremity numbness |
| Pseudoaneurysm | Transient ischemic attack (TIA) |
| Pulmonary edema | Unintended complete or incomplete AV, Sinus node, or other heart block or damage |
| Pulmonary embolism | |
| Pulmonary hypertension | Urinary retention |
| Pulmonary toxicity, like acute pulmonary syndrome | Urinary tract injury or infection related to the urinary catheter |
| Pulmonary vein dissection | Valvular damage/insufficiency |
| Pulmonary vein Stenosis | Vasovagal reactions |
| Pulmonary vein thrombus | Vision change |
| Pump failure | Volume overload |
| Renal failure | Worsening obstructive, restrictive, or other form of pulmonary disease |
| | X-ray radiation injury of skin, muscle and/or organ |

Fig. 15

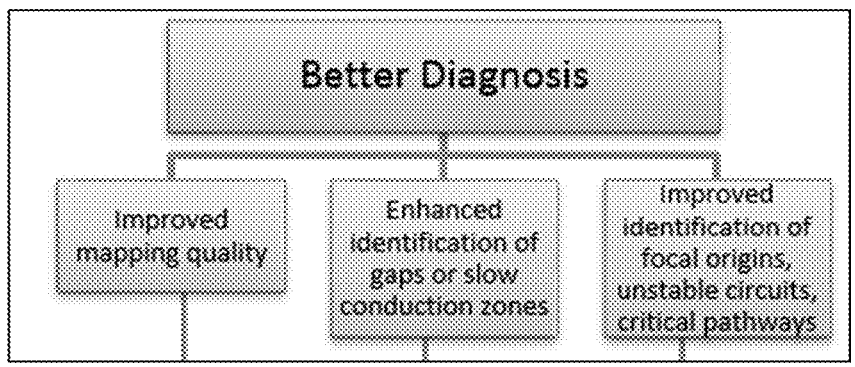
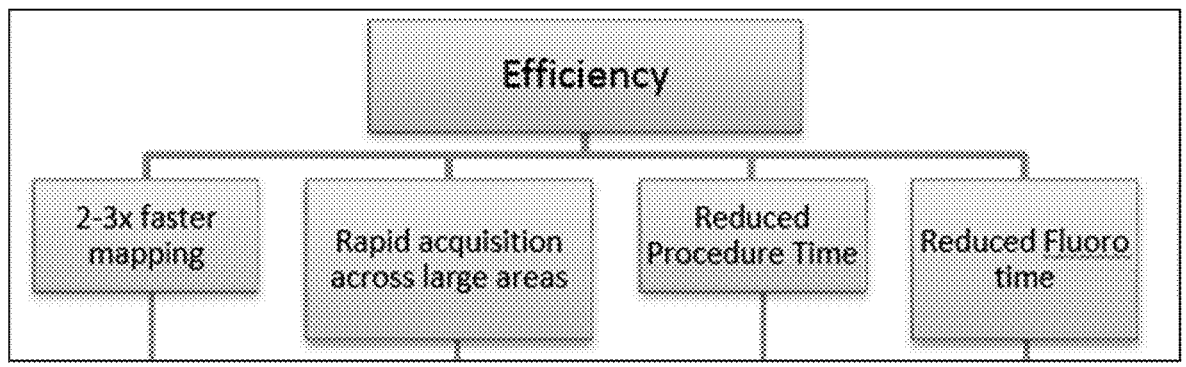
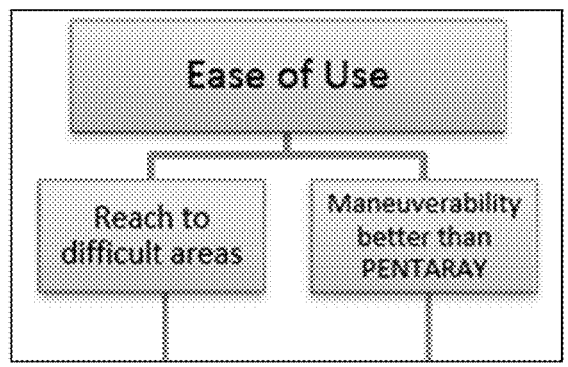
Fig. 16

| Parameters | | Catheter with Five Arms | Catheter with Eight Arms | P values |
|---|---|---|---|---|
| Point acquisition | Points per map, n (median) | 1046 ± 238 (1045) | 2178 ± 637 (2103) | ≤0.001 |
| | Mapping time, min (median) | 6.9 ± 2.7 (7.0) | 3.2 ± 0.8 (3.0) | ≤0.05 |
| | Acquisition rate, n/min (median) | 160 ± 56 (155) | 665 ± 193 (710) | ≤0.001 |
| | Catheter ectopy, PAC/sec (median) | 0.32 ± 0.15 (0.31) | 0.36 ± 0.18 (0.32) | NS |
| Voltage in healthy atria | Bipolar voltage, mV | 2.41 ± 1.92 | 1.96 ± 1.83 | ≤0.001 |
| | 5th percentile | 0.23 | 0.16 | |
| | 10th percentile | 0.36 | 0.23 | |
| | 25th percentile | 0.84 | 0.50 | |
| | Median | 1.97 | 1.39 | |
| | Unipolar voltage | 3.58 ± 1.79 | 3.49 ± 1.52 | 0.0012 |
| | 5th percentile | 1.53 | 2.00 | |
| | 10th percentile | 1.71 | 2.15 | |
| | 25th percentile | 2.14 | 2.50 | |
| | Median | 3.13 | 3.06 | |
| | Bipolar electrogram duration, msec (median) | 43 ± 13 (43) | 38 ± 12 (38) | ≤0.01 |

Fig. 17

(A) Number of Electrograms Per Map (B) Electrogram Acquisition Speed (C) Catheter-Related Ectopy Rate

|  | Normal LV | | | Post-infarct LV | | |
| --- | --- | --- | --- | --- | --- | --- |
|  | Eight arms | Five arms | p-value | Eight arms | Five arms | p-value |
| EGMs per map | 4202±962 | 2255±898 | 0.024 | 4941±1915 | 3297±1232 | 0.001 |
| Mapping time (min) | 5.3±1.0 | 12.05±2.2 | 0.015 | 14.82±7.53 | 20.37±10.95 | 0.29 |
| Acquisition rate, EGM/min | 814±126 | 148±58 | 0.015 | 355+198 | 174±84 | 0.03 |
| Acquisition density, $EGM/cm^2$ | 38±10.3 | 20.9±10.4 | 0.02 | 29.1±11.3 | 19.6±7.7 | 0.005 |
| Single beat acquisition, EGM/beat | 12.8±1.1 | 4.5±1.7 | >0.001 | 10.6±2.1 | 3.8±0.3 | 0.001 |
| Catheter induced ectopy rate (beat/min) | 13.4±2.3 | 12.4±0.7 | 0.537 | - | - | - |

Fig. 24

|  | EGM characteristics | Eight arms | Five arms | p-value |
|---|---|---|---|---|
| Electrograms in normal LV | Bipolar voltage amplitude (mV) | 4.3±2.6 | 4.5±3.2 | 0.265 |
| | 5th percentile (mV) | 1.35 | 1.31 | |
| | Median (mV) | 3.68 | 3.66 | |
| | 95th percentile (mV) | 9.4 | 10.3 | |
| | Unipolar voltage amplitude (mV) | 9.1±3.9 | 10.5±3.9 | <0.001 |
| | 5th percentile (mV) | 3.4 | 4.96 | |
| | Median (mV) | 8.7 | 10.1 | |
| | 95th percentile (mV) | 15.6 | 17.3 | |
| | Bipolar EGM Duration (msec) | 33.1±10.9 | 39.6±12.0 | 0.006 |
| Electrograms in Ventricular scar | Bipolar voltage amplitude (mV) | 1.0±0.9 | 0.9±0.8 | 0.446 |
| | 5th percentile (mV) | 0.2 | 0.2 | |
| | Median (mV) | 0.7 | 0.7 | |
| | 95th percentile (mV) | 2.7 | 2.3 | |
| | Unipolar voltage amplitude (mV) | 5.1±1.9 | 5.1±2.1 | 0.144 |
| | 5th percentile (mV) | 2.4 | 2.2 | |
| | Median (mV) | 5.2 | 5.5 | |
| | 95th percentile (mV) | 7.6 | 9 | |
| | Bipolar EGM Duration (msec) | 29.5±7.4 | 33.0±8.5 | 0.002 |
| | Abnormal EGMs in scar (%) | 52.6 | 34.2 | 0.033 |

Fig. 33

3700 placing a plurality of sensor electrodes in contact with tissue in a patient's cardiovascular system, the plurality of sensor electrodes being disposed on at least eight spines extending from a longitudinal axis
3710 processing electrical signals from some of the plurality of sensor electrodes
3720 plotting an electrocardiogram signal based on the processed electrical signals
3730 clinically improving pre-ablation mapping by maximizing contact and coverage of the catheter system within all four chambers of the heart
3730

Fig. 37

3800 placing a catheter system for mapping electrical signals generated by cardiac tissues during treatment of atrial fibrillation in a group of patients, the system including an elongated body; a distal electrode assembly comprising a proximal stem, a plurality of spines emanating from the stem; and a plurality of nonconductive spine covers, each surrounding a respective spine, wherein each spine covers one or more tensile members of the respective spine cover
3810 processing electrical signals from some of the plurality of sensor electrodes
3820 plotting an electrocardiogram signal based on the processed electrical signals
3830 clinically improving pre-ablation mapping by maximizing contact and coverage of the catheter system within all four chambers of the heart
3830

Fig. 38

3900 

```
┌─────────────────────────────────────────────┐
│ delivering a catheter system of this disclosure to one or │
│        more targeted pulmonary veins         │
│                   3910                       │
└─────────────────────────────────────────────┘
                        │
                        ▼
┌─────────────────────────────────────────────┐
│    completing improving intracardiac mapping  │
│ requirements and clinically indicated mapping with the │
│ catheter assembly, without resort to another one or more │
│              mapping catheters               │
│                   3920                       │
└─────────────────────────────────────────────┘
```

Fig. 39

4100 

```
┌─────────────────────────────────────────────┐
│ delivering a catheter system of this        │
│ disclosure to one or more targeted          │
│ pulmonary veins                             │
│ 4110                                        │
└─────────────────────────────────────────────┘
                      │
                      ▼
┌─────────────────────────────────────────────┐
│ clinically improving diagnosis of complex   │
│ atrial and ventricular arrhythmias through  │
│ simultaneous and sequential collection      │
│ intra-cardiac signals and the mapping the   │
│ heart with the catheter system              │
│ 4120                                        │
└─────────────────────────────────────────────┘
```

```
delivering a catheter system of this disclosure to one or
more targeted pulmonary veins
4210
```

```
clinically improving performance and safety of catheter
configurations as to accessibility into target areas of a
beating heart by mapping, by the catheter system, a
treatment site of the one or more targeted pulmonary veins
4220
```

Fig. 42

4300 

```
┌─────────────────────────────────────────────────┐
│ delivering a catheter system of this disclosure to one or │
│         more targeted pulmonary veins           │
│                      4310                       │
└─────────────────────────────────────────────────┘
```

```
┌─────────────────────────────────────────────────┐
│ clinically improving collection of electrode signals of the │
│ catheter system for pre-ablation mapping of a treatment site │
│       of the one or more targeted pulmonary veins │
│                      4320                       │
└─────────────────────────────────────────────────┘
```

Fig. 43

4400 delivering a catheter system of this disclosure to one or more targeted pulmonary veins
4410 clinically improving pre-ablation mapping safety, by the catheter system, as to catheter system traumaticity to cardiac tissue and thrombogenicity
4420

4500 
delivering a catheter system of this disclosure to one or more targeted pulmonary veins
4510
clinically improving pre-ablation mapping by maximizing contact and coverage of the catheter system within all four chambers of the heart
4520
Fig. 45

4600 placing a plurality of sensor electrodes of a catheter system in contact with tissue in a patient's cardiovascular system, the plurality of sensor electrodes being disposed on at least eight spines extending radially about a longitudinal axis, the catheter system including a mapping density of at least approximately 7 electrode/cm$^2$
4610 processing electrical signals from some of the plurality of sensor electrodes
4620 plotting an electrocardiogram signal based on the processed electrical signals
4630 improving mapping by maximizing contact and coverage of the catheter system within all four chambers of the heart
4640

Fig. 46

DEVICE, SYSTEM AND USE OF A
CATHETER SYSTEM TO RECORD AND
MAP CARDIAC RHYTHM

CROSS-REFERENCE TO RELATED APPLICATIONS

This application claims priority to U.S. patent application Ser. No. 16/781,952 filed Feb. 4, 2020, which claims priority to U.S. provisional patent application No. 62/815,227 filed Mar. 7, 2019, the contents of which are incorporated herein by reference in their entirety as if set forth verbatim.

FIELD

This disclosure relates to improvements in an electrophysiology catheter, in particular, a cardiac electrophysiology catheter with an electrode configuration that provides for more accurate and discrete sensing of fractionated signals.

BACKGROUND

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart which is of concern. Once the catheter is positioned within the heart, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method to record and map the electrical signals from conductive heart tissue is to percutaneously introduce an electrophysiology catheter (electrode catheter) having mapping electrodes mounted on its distal extremity. The catheter is maneuvered to place these electrodes in contact with the endocardium. By monitoring the electrical signals at the endocardium, aberrant conductive tissue sites responsible for the arrhythmia can be pinpointed.

For sensing by ring electrodes mounted on a catheter, lead wires transmitting signals from the ring electrodes are electrically connected to a suitable connector in the distal end of the catheter control handle, which is electrically connected to an ECG monitoring system and/or a suitable 3-D electrophysiology (EP) mapping system, for example, CARTO, CARTO XP or CARTO 3, available from Biosense Webster, Inc. of Irvine, Calif.

Smaller and more closely-spaced electrode pairs allow for more accurate detection of near-field potentials versus far-field signals, which can be very important when trying to treat specific areas of the heart. For example, near-field pulmonary vein potentials are very small signals whereas the atria, located very close to the pulmonary vein, provide much larger signals. Accordingly, even when the catheter is placed in the region of a pulmonary vein, it can be difficult for the electrophysiologist to determine whether the signal is a small, close potential (from the pulmonary vein) or a larger, farther potential (from the atria). Smaller and closely-spaced bipoles permit the physician to more accurately remove far field signals and obtain a more accurate reading of electrical activity in the local tissue. Accordingly, by having smaller and closely-spaced electrodes, one is able to target exactly the locations of myocardial tissue that have pulmonary vein potentials and therefore allows the clinician to deliver therapy to the specific tissue. Moreover, the smaller and closely-spaced electrodes allow the physician to determine the exact anatomical location of the ostium/ostia by the electrical signal.

Increasing electrode density (for example, by increasing the plurality of electrodes carried on the catheter) also improves detection accuracy. However, the more electrodes that are carried on the catheter, especially with higher electrode density, the risk of electrodes touching and shorting increases. Moreover, there is always the desire to improve electrode tissue contact with highly-flexible electrode assembly structures that can make contact reliably but in a manner whereby the electrode-carrying structures behave in a controllable and predictable manner without perforating or injuring tissue. As the materials used to construct these structures become more flexible and delicate, the risk of deformation and, in particular, elongation of the smaller ring electrodes and their supporting structure during catheter assembly increases. Furthermore, as electrode assembly structures become more delicate, the risk of components detaching, kinking and tangling increases.

While the success of current diagnostic catheter and mapping technologies have enabled catheter ablation therapy to become increasingly prevalent, improved intracardiac mapping tools could allow for more efficient procedures and better long-term outcomes, particularly for complex arrhythmias. For example, the one-year success rate for atrial fibrillation (AF) ablation off medications is approximately 40% to 60% for one procedure with a "70% ceiling" for three or more procedures.

Complex tachycardias are often the result of scarring in the atrial and ventricular cardiac tissue—from myocardial infarction, cardiomyopathies, previous ablation, or surgical incisions. These conditions result in necrotic and fibrotic tissue being interspersed with areas of surviving tissue, allowing for slow pathways and re-entrant circuits to form. Variable morphology and cycle lengths of these arrhythmias make it difficult to identify reentry circuits and conduction channels. Furthermore, patients that undergo catheter ablation procedures often return for repeat procedures due to pulmonary vein or linear lesions that are not durable or contiguous. Identifying these lesion gaps can be challenging.

The pathophysiology of persistent atrial fibrillation, even for initial procedures, can be complex and often involves multiple triggers outside of the pulmonary vein areas, which makes their identification and treatment difficult. Multiple studies have demonstrated that success rates of pulmonary vein isolation (PVI) are lower in patients with persistent AF. Ultimately, however, the diagnosis of local mechanisms, foci, and re-entrant circuits would enable catheter ablation treatment to be more direct and focused on the critical sites in each patient's heart. Haissaguerre and colleagues (*Right and Left Atrial Radiofrequency Catheter Therapy of Paroxysmal Atrial Fibrillation.* J Cardiovasc Electrophysiol, 1996.7(12): p. 1132-44) found that linear lesions were often arrhythmogenic due to gaps in the ablation lines and that many patients were ultimately cured with ablation of a single rapidly firing ectopic focus.

SUMMARY

The disclosure is believed to provide for an intra-cardiac signal capture device with an increased number and higher density of electrodes to facilitate more reliable identification of targets during procedures, as well as an electrophysiology catheter with closely-spaced microelectrodes for high electrode density that is believed to be clinically effective. This disclosure allows for a electrophysiology catheter having electrode-carrying structures that are delicate in construction to provide desired flexible yet be predictable in their movement upon tissue contact. The disclosure also provides for a electrophysiology catheter that is constructed in a manner that minimizes the risk of components detaching, kinking and tangling, and reinforces the spine construction to minimize deformation, including elongation of soft spine covers and of microelectrodes carried thereon.

In some examples, a catheter system is provided for high density mapping electrical signals generated by cardiac tissues before, during, and/or after the treatment of cardiac arrhythmias in a group of patients. The system can include an elongated body; a distal electrode assembly including a proximal stem and a plurality of at least eight spines emanating from the stem; and a plurality of nonconductive spine covers, each surrounding a respective spine. Each spine covers one or more tensile members of the respective spine cover. The system is configured to achieve clinically improved performance and safety of catheter configurations as to accessibility into target areas of a beating heart.

In some examples, a catheter system is provided to record and map electrical signals generated by cardiac tissues before, during, and/or after cardiac ablation procedures that treat areas of cardiac tissue that initiate and/or sustain cardiac arrhythmias. The system can include an elongated body; a distal electrode assembly including a proximal stem, a plurality of at least eight spines, a plurality of nonconductive spine covers, each spine cover surrounding a respective spine and having at least one tensile member; and a plurality of at least about 48 microelectrodes. The catheter system can be configured to maximize contact and coverage within all four chambers of the heart.

In some examples, a catheter system to record and map electrical signals generated by cardiac tissues before, during, and/or after cardiac ablation procedures treating the areas responsible for initiating and/or sustaining the cardiac arrhythmias. The system can include an elongated body; a distal electrode assembly including a proximal stem, a plurality of at least eight spines, each spine has a first section with a first preformed curvature defined by a first radius, and a linear section; a plurality of nonconductive spine covers; and a plurality of microelectrodes, at least one microelectrode carried on each spine. The catheter system is configured to clinically improve collection of electrode signals for intercardiac mapping as compared to predecessor device having less than eight spines.

In some examples, a catheter system for high density mapping electrical signals generated by cardiac tissues during ablation procedures for cardiac arrhythmias. The system can include an elongated body; a distal electrode assembly including a proximal portion; a plurality of spines, each spine having a linear taper with a wider proximal end and a narrower distal end; and a plurality of spine covers, each spine cover surrounding a respective spine. The catheter system is configured to clinically improve safety of the catheter system as to traumaticity to cardiac tissue and thrombogenicity for pre-ablation mapping.

In some examples, a catheter system to record and map electrical signals generated by cardiac tissues during treatment of a complex cardiac arrhythmia in a group of patients. The system can include an elongated body; a distal electrode assembly including a proximal stem, a plurality of at least 8 spines emanating from the stem; and a plurality of nonconductive spine covers, each surrounding a respective spine. Each spine covers one or more tensile members of the respective spine cover. The system has been shown to demonstrate statistical clinical improvement in a clinical study.

In some examples, the system is configured to clinically improve treatment of complex cardiac arrhythmias and d is configured to increase a mapping speed and density with respect to a previous mapping catheter system.

In some examples, the system is configured to record and map with at least about twice the points per map compared to a prior clinically approved mapping catheter system.

In some examples, the system is configured with a mapping time of at least about half compared to a prior clinically approved mapping catheter system.

In some examples, the system is configured with an acquisition rate of at least about twice to four times as fast compared to a prior clinically approved mapping catheter system.

In some examples, the EGM amplitude distribution at sites of ablation gaps is higher with the system.

In some examples, the system is configured for clinically improved characterization of intact ablation lines.

In some examples, the system is configured to clinically improve treatment of ischemic ventricular tachycardia; scar-related atrial tachycardia resulting from previous paroxysmal atrial fibrillation ablation or mitral valve repair procedures; and/or persistent atrial fibrillation.

In some examples, the system is configured for high-density mapping.

In some examples, the distal electrode assembly includes a higher total electrode count and density than prior mapping catheters include distal electrode assemblies with at least five spines emanating from a respective stem, resulting from the higher number electrograms acquired at each beat.

In some examples, each microelectrode of the electrode assembly includes a length of about 480 µm.

In some examples, the distal electrode assembly includes 48 platinum-iridium mapping electrodes with 6 electrodes distributed across each of the 8 spines radiating in a flower like fashion from the elongated body.

In some examples, the distal electrode assembly includes two ring electrodes on the elongated body proximate where the spine converges to aid visualization of a tip of the catheter system when used with a navigation system.

In some examples, the system also includes a navigation system for navigating the catheter system.

In some examples, the catheter system includes a plurality of different geometries, wherein a first geometry includes a plurality of 15 mm spines radiating from a distal shaft at an angle of approximately 50-65°, and wherein a second geometry includes longer 20 mm spines radiating from the distal shaft at an angle of approximately 80°.

In some examples, the catheter system is clinically validated in three different configurations, and wherein the catheter system is approximately 8.5 Fr compatible with at least about 1 biosensor and at least about 8 spines.

In some examples, the catheter system includes at least about 6 platinum and/or iridium electrodes configured for pacing and/or recording, and wherein each electrode differs in the angle and length of each spine and spacing of electrodes in a distal array.

In some examples, the system includes a predetermined success criteria of intracardiac diagnostic mapping for a population size including at least three study arrhythmia subgroups.

In some examples, the system includes a predetermined successful diagnostic mapping with the catheter for a population size including at least three study arrhythmia subgroups.

In some examples, the system includes a predetermined successful diagnostic mapping of areas of interest for a population size including at least three study arrhythmia.

In some examples, the system includes a predetermined successful use of the diagnostic catheter for a population size including at least three study arrhythmia subgroups.

In some examples, the system includes a predetermined success rate based on successful diagnostic mapping, successful use of the diagnostic catheter, and/or success criteria for a population size of at least 30 patients.

In some examples, the system includes a predetermined success rate based on successful diagnostic mapping, successful use of the diagnostic catheter, and/or success criteria for a population size of at least 300 patients.

In some examples, the system includes a predetermined success rate based on successful diagnostic mapping, successful use of the diagnostic catheter, and/or success criteria for a population size of at least 200 patients.

In some examples, the system includes a predetermined success rate based on successful diagnostic mapping, successful use of the diagnostic catheter, and/or success criteria for a population size of at least 100 patients.

In some examples, the system includes a predetermined success rate based on successful diagnostic mapping, successful use of the diagnostic catheter, and/or success criteria for a population size of at least 50 patients.

In some examples, the tensile members extend in the longitudinal direction.

In some examples, the microelectrodes on each spine are separated by a distance ranging between about 1 mm and 3 mm, as measured between leading edges of the microelectrodes.

In some examples, the microelectrodes on each spine are arranged as bipole pairs, with leading edges of microelectrodes within a pair separated by a first distance ranging between about 1 mm and 3 mm, and with leading edges of leading microelectrodes between pairs separated by a second distance ranging between approximately 1 mm and approximately 6 mm.

In some examples, the plurality of microelectrodes equals about 64.

In some examples, the plurality of microelectrodes equals about 72.

In some examples, the system also includes a first ring electrode carried on the proximal stem of the distal electrode assembly; and a second and a third ring electrodes carried on a distal portion of the elongated body.

In some examples, each microelectrode has a length ranging between about 300 μm and 500 μm.

In some examples, the microelectrodes on each spine are separated by a distance ranging between about 1 mm and 3 mm, as measured between leading edges of the microelectrodes.

In some examples, the microelectrodes on each spine are arranged as bipole pairs, with leading edges of microelectrodes within a pair separated by a first distance ranging between about 1 mm and 3 mm, and with leading edges of leading microelectrodes between pairs separated by a second distance ranging between 1 mm and 6 mm.

In some examples, each spine includes a second section with a second preformed curvature defined by a second radius different from the first radius, the second section with the second preformed curvature being distal of the first section with the first preformed curvature.

In some examples, a spine has a hinge along a lateral edge configured for in-plane deflection of the spine.

In some examples, the system also includes a sleeve circumferentially surrounding the stem.

In some examples, the spines being configured to prevent tissue from contacting a reference electrode.

In some examples, the system is configured to implement a method including placing a plurality of sensor electrodes in contact with tissue in a patient's cardiovascular system, the plurality of sensor electrodes being disposed on at least eight spines extending from a longitudinal axis; processing electrical signals from some of the plurality of sensor electrodes; plotting an electrocardiogram signal based on the processed electrical signals; and clinically improving pre-ablation mapping by maximizing contact and coverage of the catheter system within all four chambers of the heart.

In some examples, the system is configured to implement a method including placing a catheter system to record and map electrical signals generated by cardiac tissues during treatment of atrial fibrillation in a group of patients, the system including an elongated body; a distal electrode assembly including a proximal stem, a plurality of spines emanating from the stem; and a plurality of nonconductive spine covers, each surrounding a respective spine, wherein each spine covers one or more tensile members of the respective spine cover, processing electrical signals from some of the plurality of sensor electrodes; plotting an electrocardiogram signal based on the processed electrical signals; and clinically improving pre-ablation mapping by maximizing contact and coverage of the catheter system within all four chambers of the heart.

In some examples, the system is configured to implement a method including delivering a catheter system of any preceding claim to one or more targeted pulmonary veins; and completing improving intracardiac mapping requirements and clinically indicated mapping with the catheter assembly, without resort to another one or more mapping catheters.

In some examples, the system is configured to implement a method including delivering a catheter system of any preceding claim to one or more targeted pulmonary veins; and clinically improving efficiency in identification of areas of interest during pre-ablation mapping by enhancing density mapping by the catheter system over a larger area of the heart.

In some examples, the system is configured to implement a method including delivering a catheter system of any preceding claim to one or more targeted pulmonary veins; and clinically improving diagnosis of complex atrial and ventricular arrhythmias through simultaneous and sequential collection intra-cardiac signals and the mapping the heart with the catheter system.

In some examples, the system is configured to implement a method including delivering a catheter system of any preceding claim to one or more targeted pulmonary veins; and clinically improving performance and safety of catheter configurations as to accessibility into target areas of a beating heart by mapping, by the catheter system, a treatment site of the one or more targeted pulmonary veins.

In some examples, the system is configured to implement a method including delivering a catheter system of any preceding claim to one or more targeted pulmonary veins; and clinically improving collection of electrode signals of the catheter system for pre-ablation mapping of a treatment site of the one or more targeted pulmonary veins.

In some examples, the system is configured to implement a method including delivering a catheter system of any preceding claim to one or more targeted pulmonary veins; and clinically improving pre-ablation mapping safety, by the catheter system, as to catheter system traumaticity to cardiac tissue and thrombogenicity.

In some examples, the system is configured to implement a method including delivering a catheter system of any preceding claim to one or more targeted pulmonary veins; and clinically improving pre-ablation mapping by maximizing contact and coverage of the catheter system within all four chambers of the heart.

In some examples, the system includes a mapping density of at least approximately 7 electrode/cm$^2$.

In some examples, the system is configured with an average mapping time of at least approximately 3.2 minutes.

In some examples, the system is configured to generate at least approximately 4000 electrograms/map.

In some examples, the system is configured to generate at least approximately 2000 electrograms/map.

In some examples, the system is configured to generate a map comprising at least approximately 38 EGM/cm$^2$.

In some examples, the system includes an EGM acquisition rate of at least approximately 600 points/min.

In some examples, the system includes an EGM acquisition rate of at least approximately 800 points/min.

In some examples, the system includes a bipolar EGM duration of approximately 33 ms.

In some examples, the system is configured to acquire at least approximately 10 EGMs per beat.

In some examples, each microelectrode of the system is a platinum-iridium mapping electrode distributed across each of the respective spines radiating in a flower-like fashion from the elongated body.

In some examples, the microelectrodes of the system include at least about 6 platinum and/or iridium electrodes configured for pacing and/or recording, and each electrode comprising different angle, length, and spacing of electrodes in a distal array.

In some examples, the microelectrodes of the system on each spine are arranged as bipole pairs, with leading edges of microelectrodes within a pair separated by a first distance ranging between about 1 mm and 3 mm, and with leading edges of leading microelectrodes between pairs separated by a second distance ranging between approximately 1 mm and approximately 6 mm.

In some examples, the distal electrode assembly includes a first ring electrode carried on the proximal stem; and a second and a third ring electrodes carried on a distal portion of the elongated body.

In some examples, a catheter system is disclosed for high density mapping electrical signals generated by cardiac tissues before, during, and/or after the treatment of cardiac arrhythmias in a group of patients. The system can include an elongated body; a distal electrode assembly comprising a proximal stem and a plurality of at least eight spines emanating from the stem; a plurality of microelectrodes, at least one microelectrode carried on each spine; a plurality of nonconductive spine covers, each surrounding a respective spine, wherein each spine covers one or more tensile members of the respective spine cover, and wherein the system comprises an EGM acquisition rate of at least approximately 800 points/min and is configured to achieve clinically improved performance and safety of catheter configurations as to accessibility into target areas of a beating heart.

In some examples, a method is disclosed including placing a plurality of sensor electrodes of a catheter system to record and map electrical signals in contact with tissue in a patient's cardiovascular system, the plurality of sensor electrodes being disposed on at least eight spines extending radially about a longitudinal axis; processing electrical signals from some of the plurality of sensor electrodes; plotting an electrocardiogram signal based on the processed electrical signals; and clinically improving mapping by maximizing contact and coverage of the catheter system within all four chambers of the heart.

In some examples, a method is disclosed including placing a catheter system to record and map electrical signals generated by cardiac tissues during treatment of atrial fibrillation in a group of patients, the system including an elongated body; a distal electrode assembly including a proximal stem, the at least eight spines emanating from the stem; and a plurality of nonconductive spine covers, each surrounding a respective spine, wherein each spine covers one or more tensile members of the respective spine cover, processing electrical signals from some of the plurality of sensor electrodes; plotting an electrocardiogram signal based on the processed electrical signals; and clinically improving pre-ablation mapping by maximizing contact and coverage of the catheter system within all four chambers of the heart.

In some examples, a method for cardiac mapping is disclosed including delivering a catheter system of any preceding claim to one or more targeted pulmonary veins; and completing improving intracardiac mapping requirements and clinically indicated mapping with the catheter assembly, without resort to another one or more mapping catheters.

In some examples, a method for cardiac mapping is disclosed including delivering a catheter system of any preceding claim to one or more targeted pulmonary veins; and clinically improving efficiency in identification of areas of interest during pre-ablation mapping by enhancing density mapping by the catheter system over a larger area of the heart.

In some examples, a method for cardiac mapping is disclosed including delivering a catheter system of any preceding claim to one or more targeted pulmonary veins; and clinically improving diagnosis of complex atrial and ventricular arrhythmias through simultaneous and sequential collection intra-cardiac signals and the mapping the heart with the catheter system.

In some examples, a method for cardiac mapping is disclosed including delivering a catheter system of any preceding claim to one or more targeted pulmonary veins; and clinically improving performance and safety of catheter configurations as to accessibility into target areas of a beating heart by mapping, by the catheter system, a treatment site of the one or more targeted pulmonary veins.

In some examples, a method for cardiac mapping is disclosed including delivering a catheter system of any preceding claim to one or more targeted pulmonary veins; and clinically improving collection of electrode signals of the catheter system for pre-ablation mapping of a treatment site of the one or more targeted pulmonary veins.

In some examples, a method for cardiac mapping is disclosed including delivering a catheter system of any preceding claim to one or more targeted pulmonary veins; and clinically improving pre-ablation mapping safety, by the catheter system, as to catheter system traumaticity to cardiac tissue and thrombogenicity.

In some examples, a method for cardiac mapping is disclosed including delivering a catheter system of any preceding claim to one or more targeted pulmonary veins;

and clinically improving pre-ablation mapping by maximizing contact and coverage of the catheter system within all four chambers of the heart.

In some examples, a diseased heart is the intended target of the method.

In some examples, the method includes completing pre-ablation mapping for Atrial Tachycardia, re-do Paroxysmal Atrial Fibrillation or Ventricular Tachycardia by mapping an entire chamber and areas associated with targeted arrhythmias using fast anatomical mapping (FAM) (see, e.g., U.S. Pat. No. 6,400,981 for an explanation of one approach to FAM); mapping a substrate or lesion line associated with the arrhythmia identifying a conduction channel, one or more gaps and critical isthmus; and determining that mapping density at one or more areas of interests is adequate.

In some examples, the method includes minimizing acute or minimal subendocardial hemorrhages in the chambers and mitral valves by using the catheter system in eliminating or ameliorating persistent atrial fibrillation.

In some examples, the method includes demonstrating clinically improved safety and/or effectiveness of the catheter system for patients of a predetermined patient population, the predetermined patient population being divided in three different arrhythmia subgroups: Ventricular Tachycardia, complex Atrial Tachycardia or re-do Paroxysmal Atrial Fibrillation, and Persistent Atrial Fibrillation.

In some examples, the method includes at least doubling an amount of electrodes of the catheter assembly versus a prior catheter assembly within a similar footprint.

In some examples, the method includes clinically improving deployability of the catheter system to at least one of the left atrium, right atrium, left ventricle, and right ventricle.

In some examples, the method includes clinically improving deliverability of the catheter system to at least one of the left atrium, right atrium, left ventricle, and right ventricle.

In some examples, the method includes clinically improving withdrawability of the catheter system to at least one of the left atrium, right atrium, left ventricle, and right ventricle.

In some examples, the method includes clinically improving ability of the catheter system to collect at least one of unipolar and bipolar signals in at least one of the left atrium, right atrium, left ventricle, and right ventricle.

In some examples, the method includes clinically improving maneuverability of the catheter system within at least one of the left atrium, right atrium, left ventricle, and right ventricle.

In some examples, the method includes clinically improving electrode contact of the catheter system with cardiac tissue.

In some examples, the method includes clinically improving at least one of electrode spacing and electrode array coverage of the catheter system.

In some examples, the method includes providing feedback evaluating maneuverability and handling, pacing, unipolar and/or bipolar signal quality, workflow, visualization, and catheter interactions.

In some examples, the method includes clinically improving, by the catheter system, bipolar signal quality.

In some examples, the method includes clinically improving, by the catheter system, unipolar signal quality.

In some examples, the method includes filtering out non-chamber atrial signals.

In some examples, the step of mapping the substrate or lesion line associated with the arrhythmia further includes local activation mapping required for complex AT and VT procedures.

In some examples, the step of mapping the substrate or lesion line associated with the arrhythmia further includes voltage mapping for re-do PAF and VT procedures.

In some examples, the area of interest includes one or more slow conduction zones.

In some examples, mapping density is adequate when target data interpolation is between points≤5 mm.

In some examples, the method includes completing pre-ablation mapping when the atrium is completely mapped using a FAM (Fast Anatomical Mapping) algorithm.

In some examples, the method includes completing pre-ablation mapping when the atrium is completely mapped using a 4D Local Activation Time mapping algorithm for an entire left atrium and/or right atrium.

In some examples, the method includes positioning the catheter assembly in a location to maximize contact with the endocardium; and taking 30-second 4D LAT recordings in succession until the entire atrium is mapped.

In some examples, the method includes deploying the catheter system in all four chambers of the heart using a transvenous, transseptal, or retrograde transaortic approach to map atrial and ventricular tachyarrhythmias.

In some examples, the method includes creating clinically improved high density 3D local activation map for paroxysmal atrial fibrillation and 4D activation map for persistent atrial fibrillation.

In some examples, the method includes creating clinically improved high density voltage maps for atrial or ventricular substrates.

In some examples, the method includes simultaneously collecting sensory information from up to 48 electrodes of the distal electrode assembly, each spine comprising approximately six electrodes; and clinically enhancing mapping of cardiac arrhythmias with a navigation system operatively connected to the catheter assembly.

In some examples, the method includes alternating inter-electrode spacing between 2 and 6 mm with the number of closely spaced bipoles increased to approximately 24.

In some examples, the method includes clinically improving pre-ablation mapping time, including types and numbers of areas of interest captured with the catheter system in pre-ablation mapping.

In some examples, the types and numbers of areas of interest comprise Pulmonary Vein triggers, previous Pulmonary Vein Isolation lesion gaps, ventricular scar slow conduction zone, critical isthmus for atypical flutter, focal and rotational activation patterns only for Persistent Atrial Fibrillation procedures.

In some examples, the method includes clinically improving pre-ablation mapping duration, including time for FAM only and total time by chamber and arrhythmia subgroup with the catheter assembly.

In some examples, the method includes clinically improving pre-ablation mapping duration. In some examples, pre-ablation mapping duration is defined by total procedure and mapping time.

In some examples, the method includes increasing an amount of bipolar electrograms recorded at each beat by the catheter system from approximately 10 to approximately 40.

In some examples, the method includes increasing, as compared to another clinically approved catheter system comprising a plurality of sensor electrodes being disposed on approximately five spines extending from a longitudinal axis, an amount of bipolar electrograms by a magnitude of two or more recorded at each beat by the catheter system comprising the at least eight spines.

In some examples, the catheter system of the method includes a mapping density of at least approximately 7 electrode/cm$^2$.

In some examples, the method includes increasing, as compared to another clinically approved catheter system comprising a plurality of sensor electrodes being disposed on approximately five spines extending from a longitudinal axis, a mapping density (electrode/cm$^2$) by a magnitude of approximately three or more by the catheter system comprising the at least eight spines.

In some examples, the method includes decreasing, as compared to another clinically approved catheter system comprising a plurality of sensor electrodes being disposed on approximately five spines extending from a longitudinal axis, an average mapping time by at least approximately 50%.

In some examples, the catheter system of the method includes an average mapping time of at least approximately 3.2 minutes.

In some examples, the method includes increasing, as compared to another clinically approved catheter system comprising a plurality of sensor electrodes being disposed on approximately five spines extending from a longitudinal axis, electrograms/map by a magnitude of approximately two or more by the catheter system comprising the at least eight spines.

In some examples, the catheter system of the method is configured to generate at least approximately 2000 electrograms/map.

In some examples, the catheter system of the method is configured to generate at least approximately 4000 electrograms/map.

In some examples, the method includes increasing, as compared to another clinically approved catheter system comprising a plurality of sensor electrodes being disposed on approximately five spines extending from a longitudinal axis, an EGM acquisition rate (points/min) by a magnitude of approximately four or more by the catheter system comprising the at least eight spines.

In some examples, the catheter system of the method includes an EGM acquisition rate of at least approximately 600 points/min.

In some examples, the catheter system of the method includes an EGM acquisition rate of at least approximately 800 points/min.

In some examples, the method includes decreasing, as compared to another clinically approved catheter system comprising a plurality of sensor electrodes being disposed on approximately five spines extending from a longitudinal axis, bipolar and unipolar amplitudes.

In some examples, the catheter system of the method includes a bipolar EGM duration of approximately 38 ms.

In some examples, the method includes generating, by the catheter system, a map comprising at least approximately 38 EGM/cm$^2$.

In some examples, the method includes increasing, as compared to another clinically approved catheter system comprising a plurality of sensor electrodes being disposed on approximately five spines extending from a longitudinal axis, a higher proportion of near-field local abnormal ventricular activities by a magnitude of approximately 1.5 or more by the catheter system comprising the at least eight spines.

In some examples, the method includes detecting, by the catheter system, at least approximately 50% of near-field local abnormal ventricular activities.

In some examples, the catheter system of the method is configured to acquire at least approximately 10 EGMs per beat.

In some examples, the method includes generating a map, by the catheter system, with an overall mapping time of approximately 5 minutes.

In some examples, a method is disclosed, including placing a plurality of sensor electrodes of a catheter system in contact with tissue in a patient's cardiovascular system, the plurality of sensor electrodes being disposed on at least eight spines extending radially about a longitudinal axis, the catheter system comprising a mapping density of at least approximately 7 electrode/cm$^2$; processing electrical signals from some of the plurality of sensor electrodes; plotting an electrocardiogram signal based on the processed electrical signals; and improving mapping by maximizing contact and coverage of the catheter system within all four chambers of the heart.

In some examples, inclusion criteria for patients of the method includes

Diagnosed and is a candidate for clinically-indicated catheter ablation procedure for the management of ischemic ventricular tachycardia—OR—complex atrial tachycardia/atypical atrial flutter/paroxysmal atrial fibrillation following a pulmonary vein isolation ablation or mitral valve repair procedure, —OR—persistent atrial fibrillation;

Age 18 years or older;

Signed Patient Informed Consent Form (ICF); and

Able and willing to comply with all pre-, post-, and follow-up testing and requirements.

In some examples, includes exclusion criteria for patients of the method comprise:

History of continuous AF sustained longer than 12 months;

History of AF<7 days and no previous AF ablation procedure;

Previously diagnosed with long-standing persistent atrial fibrillation;

Previously diagnosed with idiopathic PVC/VT;

Study arrhythmia secondary to reversible cause;

Atrial arrhythmias: patients with a left atrial size>55 mm;

LVEF≤25% for VT patients;

LVEF≤40% for AF patients;

Documented thrombus in the chamber to be mapped by the study catheter on imaging;

Contraindication to anticoagulation (e.g. heparin, warfarin, dabigatran);

History of blood clotting or bleeding abnormalities (e.g. hypercoagulable state);

Myocardial infarction within the past 2 months (60 days);

Documented thromboembolic event (including TIA) within the past 12 months (365 days);

Uncontrolled heart failure or NYHA function class III or IV;

Implanted with a pacemaker or intracardiac cardiac defibrillator within the past 3 months (90 days);

Implanted with a prosthetic valve;

Active systemic infection;

Diagnosed atrial or ventricular myxoma;

Implanted with an interatrial baffle or patch;

Atrial septal closure within the past 6 weeks (42 days);

Presence of a condition that precludes vascular access;

Presence of intramural thrombus, tumor or other abnormality that precludes catheter introduction or manipulation;

Women who are pregnant (as evidenced by pregnancy test if pre-menopausal); and

Enrollment in an investigational study evaluating another device or drug.

To the accomplishment of the foregoing and related ends, certain illustrative aspects are described herein in connection with the following description and the appended drawings. These aspects are indicative, however, of but a few of the various ways in which the principles of the claimed subject matter can be employed and the claimed subject matter is intended to include all such aspects and their equivalents. Other advantages and novel features can become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 6A depicts three descriptions of the configurations of the exemplary catheters of this disclosure.

FIG. 6B depicts three descriptions of the configurations of the exemplary catheters of this disclosure.

FIG. 8 is a table summarizing features used in the system of FIG. 7.

FIG. 9 shows a schematic overview of the study of this disclosure.

FIG. 10 is a table summarizing the schedule for subject treatments and evaluations.

FIG. 11 shows a table summarizing intensity or severity of each AE assessed according to classifications.

FIG. 12 shows a table summarizing adverse event causality classifications.

FIG. 13 shows a table summarizing adverse event outcome classifications.

FIG. 14 shows a table summarizing anticipated adverse events.

FIG. 15 shows a table summarizing additional anticipated adverse events.

FIG. 16 shows a graphical overview of certain endpoints of the study and corresponding factors.

FIG. 17 is a table summarizing electrogram acquisition and performance measures in the healthy atria of the second study of this disclosure.

FIG. 24 is a table summarizing difference in mapping performance between the catheters in healthy and infarcted myocardium in the third study.

FIG. 33 is a table summarizing the unipolar and bipolar EGM characteristics in the third study.

FIG. 37 depicts a graphical overview of one method according to this disclosure.

FIG. 38 depicts a graphical overview of one method according to this disclosure.

FIG. 39 depicts a graphical overview of one method according to this disclosure.

FIG. 41 depicts a graphical overview of one method according to this disclosure.

FIG. 42 depicts a graphical overview of one method according to this disclosure.

FIG. 43 depicts a graphical overview of one method according to this disclosure.

FIG. 45 depicts a graphical overview of one method according to this disclosure.

FIG. 46 depicts a graphical overview of one method according to this disclosure.

DETAILED DESCRIPTION

Figure 1:
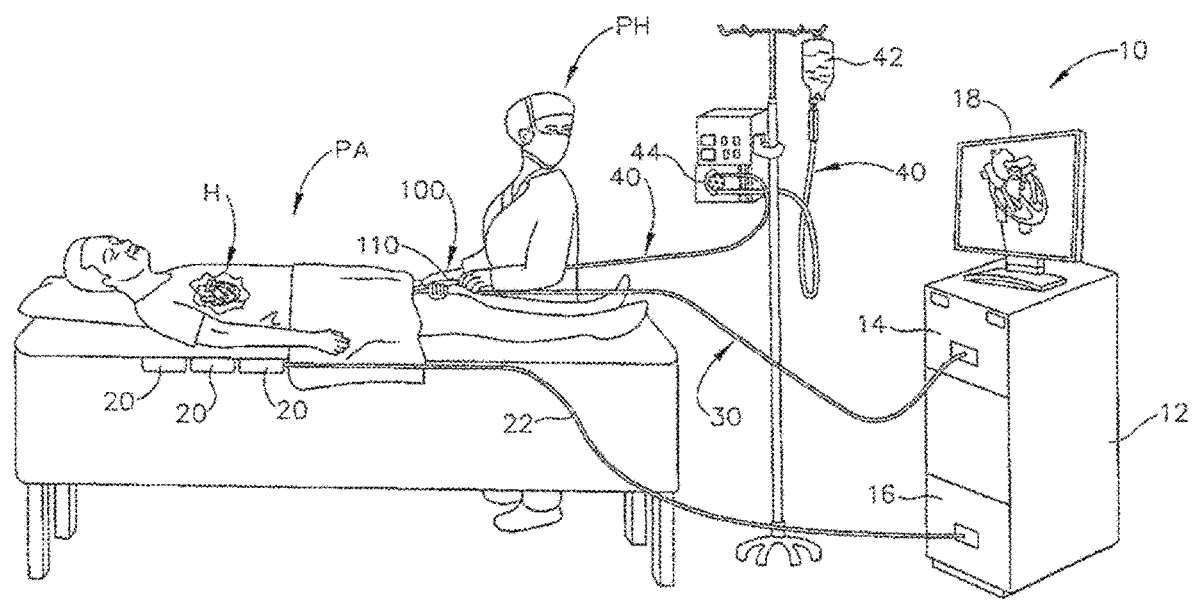
FIG. 1 depicts a schematic view of a medical procedure in which a catheter of this disclosure used in an example procedure of the study of this disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values±10% of the recited value, e.g. "about 90%" can refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, or any other individual or delivery instrumentation associated with delivery of a multi-electrode RF balloon catheter for the treatment of drug refractory atrial fibrillation to a subject. As discussed herein, the term "safety", as it relates to devices used in ablating cardiac tissue, related delivery systems, or method of treatment refers to a relatively low severity of adverse events, including adverse bleeding events, infusion or hypersensitivity reactions. Adverse bleeding events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration, EMEA or a corresponding national regulatory agency. For example, a clinical study can be an adequately sized, randomized, double-blinded controlled study used to clinically prove the effects of the cardiac ablation device(s) and related system(s) of this disclosure. Most preferably to clinically prove the effects of the device(s) with respect to all targeted pulmonary veins, for example, to achieve a clinically effective outcome in for the patient and/or achieve pulmonary vein isolation in those afflicted veins.

As discussed herein, the term "computed tomography" or CT means one or more scans that make use of computer-processed combinations of many X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

Certain risks and hazards can be common to catheter-based cardiac mapping procedures, as follows:

Allergic reaction: to the local anesthetic, sedatives, X-ray dye, heparin, protamine, or other agents administered during the procedure (risk<1%);

Arterial or venous injury: including arterial dissection, thrombosis, occlusion or hemorrhage at the catheter insertion sites or at other sites along the vessels (risk<1%). These types of injuries may cause hemorrhage, hematoma, or ischemic injury to an extremity or major organ. Hemorrhage as a result of anticoagulation (risk<0.5%), which may require transfusion;

Entanglement/and or entrapment. When a catheter is within the proximity of the tricuspid valve or mitral valve, cautions need to be applied to avoid entanglement with chordae tendinae.

Infection: The percutaneous procedure carries risk of infection, either at the catheter insertion site or systemically, including endocarditis and septic emboli (risk<0.5%). This risk can be minimized by using standard aseptic technique and, when indicated, by the use of antibiotic agents.

Radiation exposure: Radiation exposure during the fluoroscopic imaging of the catheters may result in an increase in the lifetime risk of developing a fatal malignancy (0.1%) or a genetic defect in offspring (0.002%).

The present disclosure is related to systems, methods and devices to record and map and ablating cardiac tissue to treat cardiac arrhythmias. In particular, a catheter assembly of this disclosure is a multi-electrode mapping catheter designed with a higher total electrode count and density than prior mapping catheters. In some examples, the catheter can employ 48 platinum-iridium mapping electrodes, with 6 electrodes distributed across each of the 8 spines radiating in a flower-like fashion from the main shaft. The catheter is intended to be deployed in the heart chambers through a commercially available sheath and utilizing a corresponding navigation system. The catheter and navigation system are intended to maximize contact and coverage within all four chambers of the heart. In some embodiments, the catheter can have two ring electrodes on the shaft proximate where the spines converge, to aid visualization of the tip when used with the navigation system.

Figure 2:
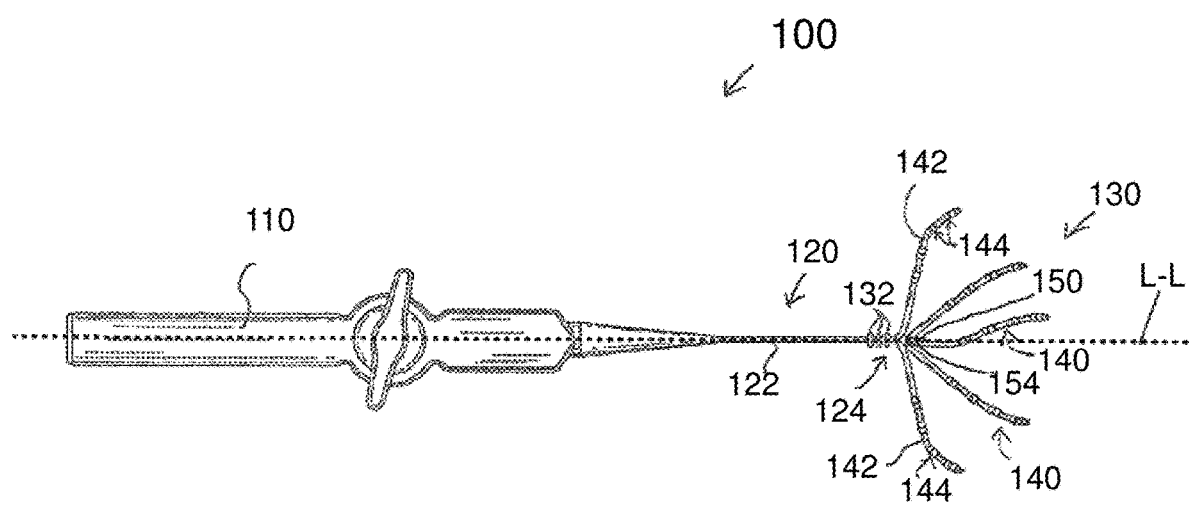
FIG. 2 depicts a top plan view of the catheter assembly of FIG. 1.

FIGS. 1 and 2 show an exemplary medical procedure and associated components of a cardiac EP mapping catheter system that may be used to record and map. In particular, FIG. 1 shows a physician (PH) grasping a handle (110) of a catheter assembly (100), with an end effector (130) of a catheter (120) of catheter assembly (100) disposed in a patient (PA) to perform EP mapping in or near the heart (H) of the patient (PA) with a processing system (10) that includes a console (12) with a mapping or ablating module (14) and a location module (16). Catheter assembly (100) with system unit (10) can be understood as including features more clearly described in Appendix 1 which includes U.S. application Ser. No. 15/890,318, U.S. Pat. Nos. 5,558, 091; 6,177,792; 6,690,963; 6,788,967; 5,944,022; 5,983, 126; 6,456,864; 5,391,199; 5,443,489; and 6,172,499; each of which are incorporated by reference in their entirety as if set forth verbatim herein.

As shown in FIG. 2, catheter (120) includes an elongate flexible shaft (122), with end effector (130) being disposed at a distal end (124) of shaft (122). End effector (130) and variations thereof will be described in greater detail below. Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath the patient (PA) and are coupled with guidance and drive system (10) via another cable (22). Field generators (20) are also merely optional.

Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (132, 146, 148, 154) of end effector (130) as described in greater detail below. Console (12) includes a processor (not shown) that processes such EP mapping signals and thereby provides EP mapping as is known in the art. In addition, or in the alternative, first driver module (14) may be operable to provide RF power to electrodes (132, 146, 148) of end effector (130) to thereby ablate tissue. In some versions, first driver module (14) is also operable to receive position indicative signals from a position sensor (not shown) in end effector (130), as will be described in greater detail below. In such versions, the processor of console (12) is also operable to process the position indicative signals from the position sensor to thereby determine the position of the end effector (130) of catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H). Some versions of end effector (130) include a position sensor (not shown) that is operable to generate signals that are indicative of the position and orientation of end effector (130) within the patient (PA). Each position sensor may include a wire coil or a plurality of wire coils (e.g., three orthogonal coils) that are configured to generate electrical signals in response to the presence of an alternating electromagnetic field generated by field generators (20). Other components and techniques that may be used to generate real-time position data associated with end effector (130) may include tissue impedance sensing, wireless triangulation, acoustic tracking, optical tracking, inertial tracking, and the like. By way of example only, position sensing may be provided in accordance with at least some of the teachings of the attached U.S. Pat. Nos. 5,944, 022; 5,983,126; 6,456,864; 5,443,489; 5,558,091; 6,172, 499; 6,177,792; 6,690,963; 6,788,967 (with a copy of each in the Appendix 1), the disclosure of which is incorporated by reference herein. Alternatively, end effector (130) may lack a position sensor.

Turning back to FIG. 1, display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from the position sensor of end effector (130). For instance, as end effector (130) of catheter (120) moves within the patient (PA), the corresponding position data from the position sensor may cause the processor of console (12) to update the patient anatomy views in display (18) in real time to depict the regions of patient anatomy around end effector (130) as end effector (130) moves within the patient (PA). Moreover, the processor of console (12) may drive display (18) to show locations of aberrant conductive tissue sites, as detected via EP mapping with end effector (130). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (130) on the images of the patient's anatomy, such as by superimposing an illuminated dot, a crosshair, a graphical representation of end effector (130), or some other form of visual indication. Such a superimposed visual indication may also move within the images of the patient anatomy on display (18) in real time as the physician moves end effector (130) within the patient (PA), thereby providing real-time visual feedback to the operator about the position of end effector (130) within the patient (PA) as end effector (130) moves within the patient (PA). The images provided through display (18) may thus effectively provide a video tracking the position of end effector (130) within a patient (PA), without necessarily having any optical instrumentation (i.e., cameras) viewing end effector (130). In the same view, display (18) may simultaneously visually indicate the locations of aberrant conductive tissue sites detected through the EP mapping as described herein. The physician (PH) may thus view display (18) to observe the real time positioning of end effector (130) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (130) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

Figure 3:
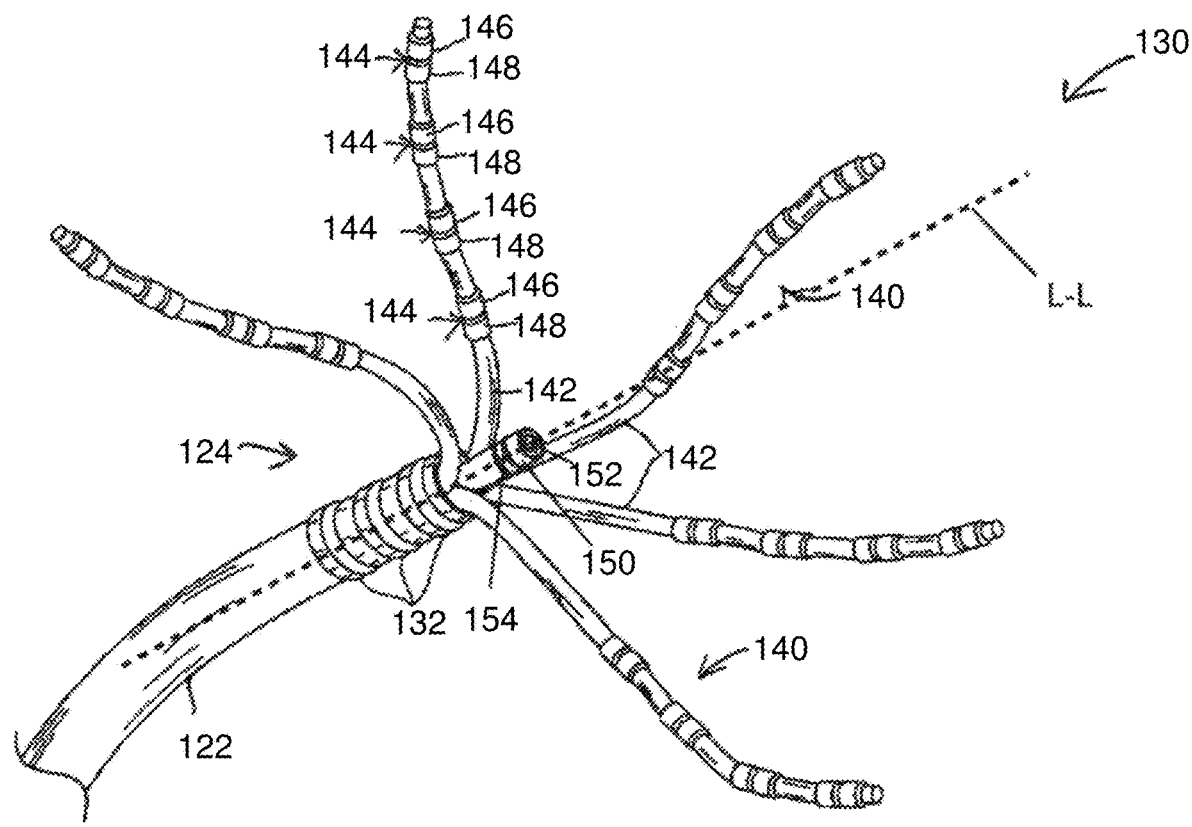
FIG. 3 depicts a perspective view of the end effector of the catheter assembly of FIG. 2.

FIGS. 2-3 show end effector (130) in greater detail. In addition to the following, end effector (130) and other aspects of catheter assembly (100). As shown, end effector (130) of the present example includes a set of spines or arms (140) extending distally from the distal end of catheter shaft (122). Arms (140) radiate generally outwardly away from the central longitudinal axis (L-L) of catheter shaft (122). In the present example, end effector (130) has five arms (140).

Figure 4:
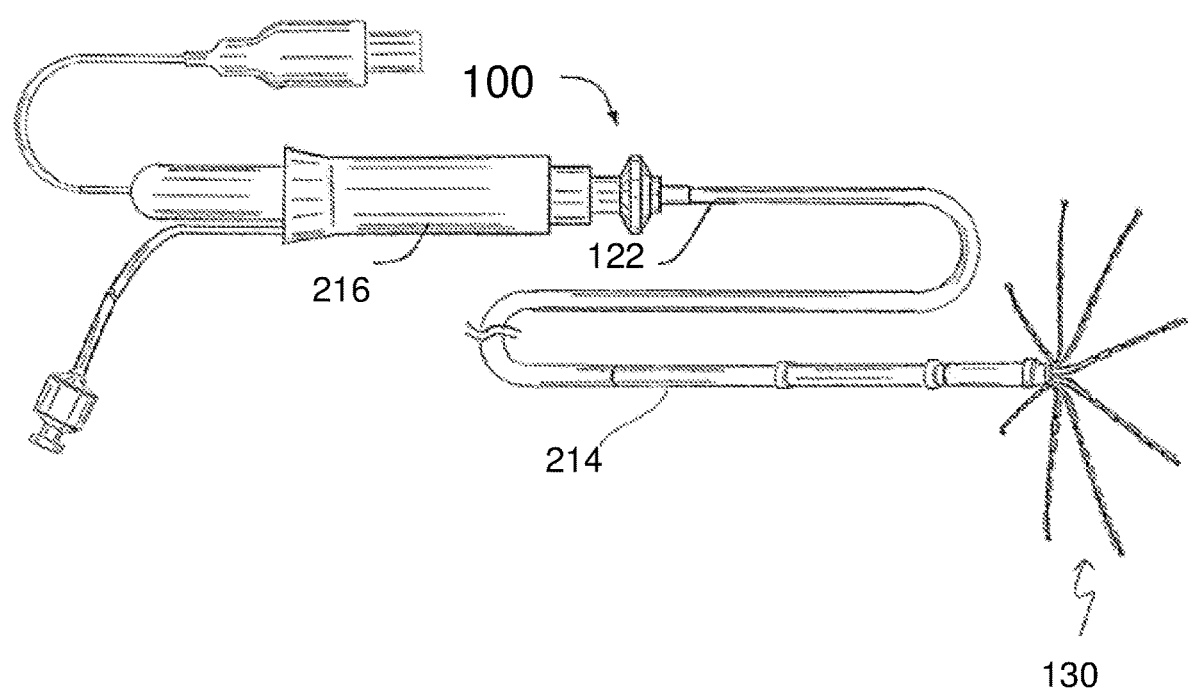
FIG. 4 is a perspective view of a catheter of the present invention, according to one embodiment.
Figure 5:
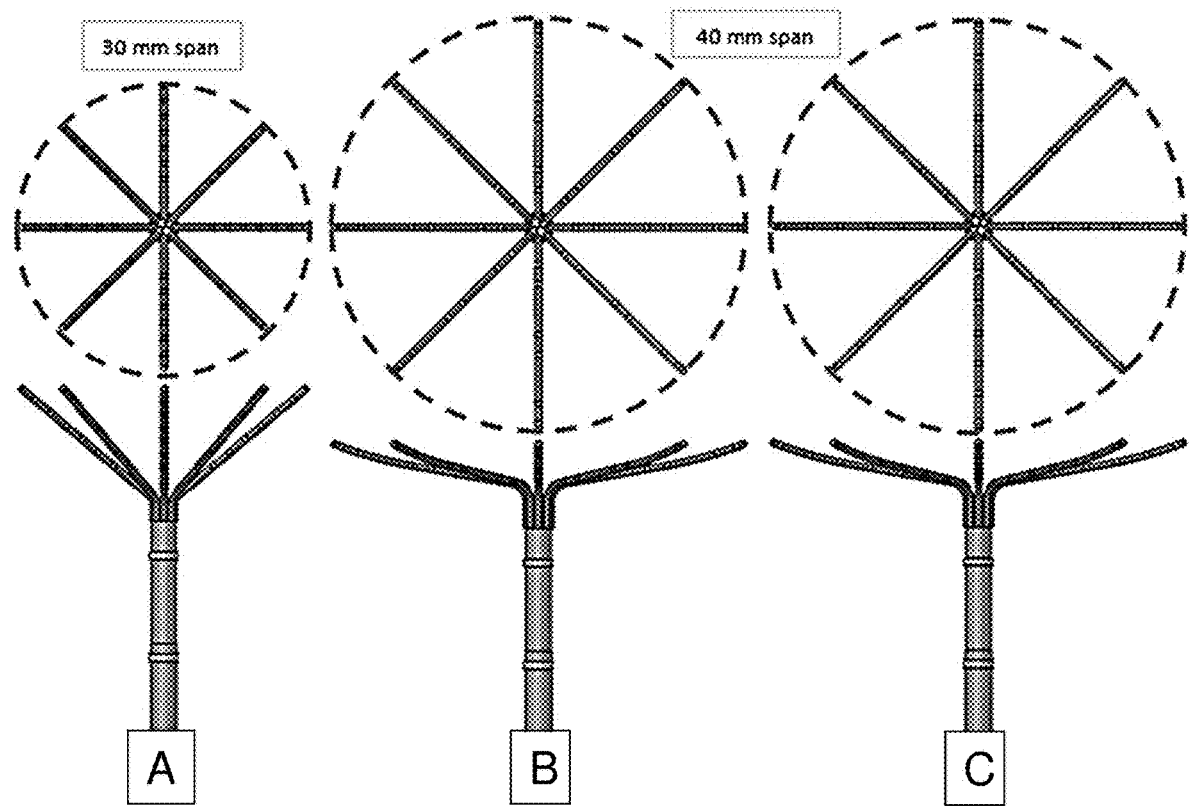
FIG. 5 depicts three configurations of exemplary catheters of this disclosure.

In some other versions, end effector (130) has eight arms (140) (see, e.g., FIG. 4 and FIG. 5). Alternatively, end effector (130) may have any other suitable number of arms (140).

Each arm (140) includes a flexible elongate body (142) with a respective set of longitudinally spaced ring electrode (146, 148) pairs. Each arm (140) distally terminates in a respective free end. In the present example, each arm (140) has four pairs of electrodes (146, 148). Alternatively, more or fewer than four pairs of electrodes (146, 148) may be provided on each arm (140). The electrodes (146, 148) of each pair are separated from each other by a corresponding gap (144). In the present example, each pair of electrodes (146, 148) is configured to provide bipolar sensing of electrocardiogram signals as electrodes (146, 148) are placed in contact with cardiovascular tissue. Each pair of electrodes (146, 148) may also be used to provide unipolar sensing; or only a single electrode (146, 148) of each pair may be used to provide unipolar sensing while the other electrode (146, 148) of the pair is not used. Catheter assembly (100) may also enable the physician (PH) to toggle end effector (130) between two or more modes, including a bipolar sensing mode and a unipolar sensing mode. In some other variations, electrodes (146, 148) are not provided in pairs, such that each arm (140) only has either an array of electrodes (146) or an array of electrodes (148).

End effector (130) further includes a longitudinally spaced array of ring electrodes (132) at the distal end (124) of catheter shaft (122), proximal to arms (140). Electrodes (132) may also be configured to cooperate in pairs to provide bipolar sensing of electrocardiogram signals as electrodes (132) are placed in contact with cardiovascular tissue. Alternatively, one or more of electrodes (132) may be used to provide unipolar sensing. In some other versions, one or all of electrodes (132) are omitted.

End effector (130) further includes a central shaft (150) protruding distally from distal end (124) of catheter shaft (122), near the proximal ends of arms (140). Central shaft (150) is coaxially aligned with catheter shaft (122) and defines a distal opening (152), which is in communication with a lumen formed along the length of central shaft (150). This lumen is in fluid communication with fluid conduit (40), which is further in communication with fluid source (42) as described above. Central shaft (150) is thus operable to dispense irrigation fluid (e.g., saline) from fluid source (42) to a site within a patient (PA) (e.g., within a cardiovascular structure) via distal opening (152). In some other versions, central shaft (150) lacks distal opening (152) and is unable to otherwise dispense irrigation fluid.

Central shaft (150) of the present example further includes a ring electrode (154), which is configured to serve as a reference electrode as will be described in greater detail below. Ring electrode (154) is positioned to contact blood when end effector (130) is located within a cardiovascular structure in a patient (e.g., in the pulmonary vein, etc.). However, arms (140) are also configured to prevent ring electrode (154) from contacting tissue while end effector (130) is disposed in a cardiovascular structure. Thus, during normal use, one or more electrodes (146, 148) will contact tissue while ring electrode (154) does not contact tissue.

While ring electrode (154) may not contact the tissue surface, ring electrode (154) will nevertheless contact blood flowing through the cardiovascular system. If end effector (130) is positioned in the pulmonary vein, for example, one or more electrodes (146, 148) may contact the tissue surface while ring electrode (154) contacts blood flowing through the pulmonary vein. The one or more electrodes (146, 148)

contacting the tissue surface may pick up electrical potentials at the contacted regions of the tissue surface, while ring electrode (154) picks up a reference potential from the blood in which ring electrode (154) is disposed. The processor of console (12) may process the potentials from electrodes (146, 148, 154) and thereby provide an electrocardiogram signal. Such electrocardiogram signals may be used to provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue. Catheter assembly (100) can also include different geometries. For example, one geometry can include a plurality of 15 mm spines radiating from the distal shaft at an angle of 50-65°. Another configuration includes longer 20 mm spines radiating from the distal shaft at an angle of approximately 80°.

Referring to FIG. 4, catheter assembly (100) is shown with elongate shaft (122) (e.g., catheter body), an intermediate deflection section (214), end effector assembly (130), and a control handle (216) proximal of the catheter assembly (100). Catheter assembly (100) as described can be flexible, tubular and having a single, axial or central lumen. The catheter can be of any suitable construction and made of any suitable material. A presently preferred construction comprises an outer wall made of a polyurethane, or PEBAX. The outer wall can be an imbedded braided mesh of high-strength steel, stainless steel or the like to increase torsional stiffness of the catheter body so that, when the control handle (216) is rotated, the deflection section (214) rotates in a corresponding manner.

Figure 7:
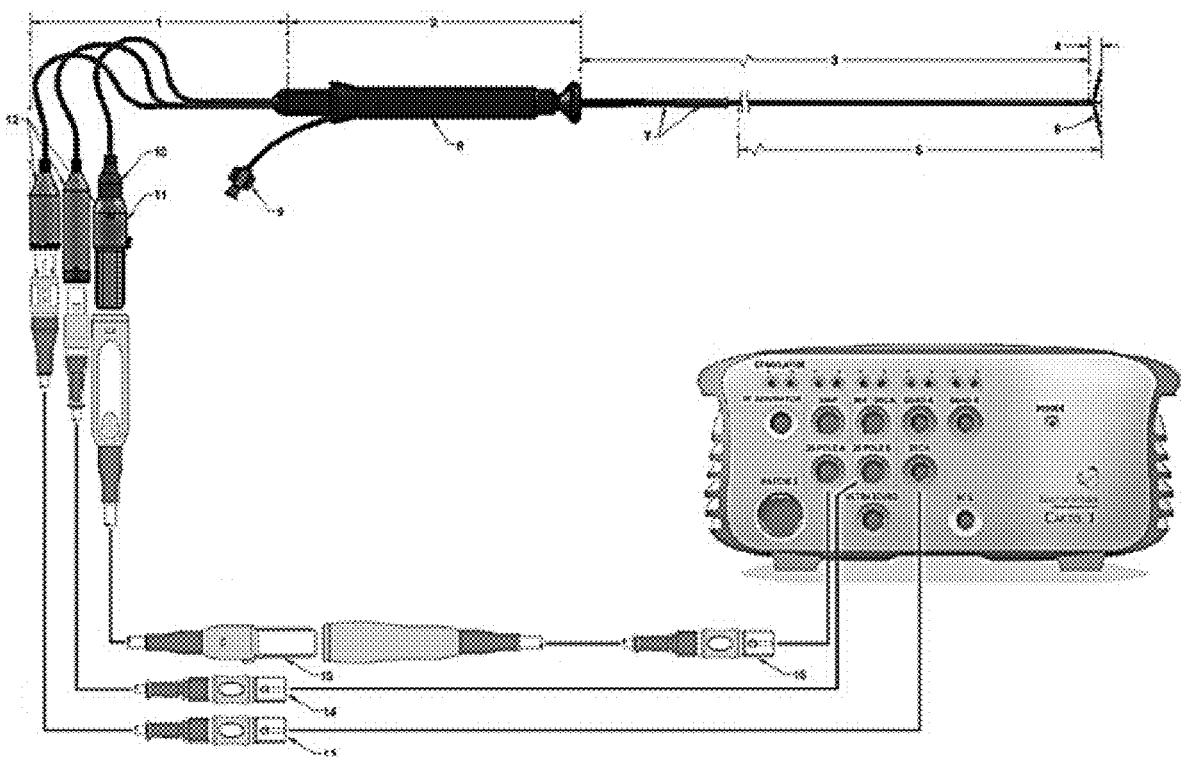
FIG. 7 depicts a connectivity diagram of an exemplary catheter with corresponding cables to an example patient user interface.

FIG. 5 is a graphical depiction of the three example configurations of the catheter assembly used in the studies of this disclosure. FIGS. 6A-6B summarize the three configurations in chart form, including spine length, shaft diameter size, curve type, electrode spacing, coverage area, count, bipolar channels, unipolar channels, size and density. FIG. 7 depicts a connectivity diagram of an exemplary catheter assembly with corresponding cables to an example patient user interface. FIG. 8 is a table summarizing features used in the system of FIG. 9. Each site of the studies of this disclosure included the catheter assembly (100) whereby features of assembly (100) described herein were used for the ablation procedure and provided for in the study protocol.

Overview of the First Study

This disclosure is more clearly understood with a corresponding first study discussed more particularly below with respect to mapping and/or treatment of PAF. FIG. 9 provides a schematic overview of the subject study protocol of this disclosure, which is attached hereto in Appendix 2 and incorporated by reference in its entirety as if set forth verbatim herein. As can be seen, the study investigated clinical safety and effectiveness of the catheter assembly of this disclosure to record and map a treatment site during the isolation of the atrial pulmonary veins in treatment of subjects with drug refractory, symptomatic, and paroxysmal atrial fibrillation. This study was a prospective, single arm, non-randomized, open-label, multi-center study. 30 subjects were included with a target of equal numbers of subjects (n=10) among the three study arrhythmia subgroups will be enrolled. In the study, the herein described catheter was validated in three different configurations whereby all three versions were 8.5 Fr compatible catheters with 1 biosensor and 8 spines. Each catheter included 6 platinum/iridium electrodes that could be used for pacing and/or recording whereby each was distinguished by the angle and length of each spine and spacing of electrodes in the distal array. During study procedures, investigators used catheter assembly (100) in place of the other standard diagnostic catheter choice (e.g. LASSO® Catheter or PENTARAY® Catheter) for the study qualifying arrhythmia. Any use of a commercial mapping catheter in place of catheter assembly (100) was considered as failure of the primary study endpoint.

During the study, the physician mapped the chamber of interest with catheter assembly (100) prior to a standard of care ablation procedure. Pre-ablation mapping for AT, re-do PAF or VT was considered complete when all of the following were accomplished, as applicable:

the entire chamber and areas associated with the targeted arrhythmia(s) were completely mapped using fast anatomical mapping (FAM);

Substrate or previous lesion line associated with the arrhythmia(s) was mapped;

Local activation mapping required for complex AT and VT procedures;

Voltage mapping required for re-do PAF and VT procedures;

Conduction channel, gap(s) and critical isthmus were identified (as applicable); and Mapping density at the areas of interests (e.g. slow conduction zones) was adequate (target data interpolation between points≤5 mm)

PsAF pre-ablation mapping was considered complete when the atrium was completely mapped using the FAM algorithm and the 4D LAT algorithm is used to map the entire left atrium (and right atrium, if applicable). Catheter assembly (100) was positioned to maximize contact with the endocardium and 30-second 4D LAT recordings were taken in succession until the entire atrium was mapped.

FIG. 10 is a table summarizing the schedule for subject treatments and evaluations. In the study, standard of care assessments were performed before ICF signature. Informed consent was signed within the 60 days prior to procedure. Medical history included arrhythmia, heart disease and thromboembolic events as well as other information. TTE was used to determine the LA size atrial procedures and LVEF % for all procedures within the 30 days prior to procedure. If the subject had undergone a TTE in the last 6 months where the requested values were assessed, the assessment was not required. Pregnancy tests were administered for women of child-bearing potential only within the 7 days prior to procedure. Thrombus detection was done 1 day prior to the procedure or the day of the study procedure in order to rule out the presence of thrombus using one of the following modalities TEE, ICE, CT, MRI. AEs were collected from the time the subject signs the informed consent onward.

FIG. 11 shows a table summarizing intensity or severity of each AE assessed according to classifications. For purposes of this disclosure, an AE can be any undesirable experience (sign, symptom, illness, abnormal laboratory value, or other medical event) occurring to a subject during the course of the study, whether or not it is related to the device or procedure. Physical findings (including vital signs) observed at follow-up, or preexisting physical findings that worsen compared to baseline, are adverse events if the investigator determines they are clinically significant. As to the study, any medical condition present at the time that the subject is screened is considered as baseline and not reported as an AE. Such conditions should be added to background medical history, if not previously reported. However, if the study subject's condition deteriorates at any time during the study, it can be recorded as an AE.

Similarly, adverse events can be considered if any of the following apply: an event is cardiovascular in nature, the event is a serious adverse event, causality is related to investigational device, ablation procedure, or unknown in nature. In contrast, the following clinical events were not considered an adverse event for this study: minor pericarditis attributable to the ablation procedure defined as pleuritic chest discomfort with or without pericardial rub and ECG changes, AF/AFL/AT recurrence requiring pharmacological or synchronized electrical cardioversion during the hospitalization for the index ablation procedure, or throughout the duration of the study. However, new onset of left atrial flutter occurring post-ablation is an AE, and re-ablation for AF or pre-existing AFL/AT itself is not an AE, however any procedural complication is considered an AE and shall be reported within the applicable timelines.

A serious adverse event (SAE) in this disclosure were those considered any event that meets one or more of the following criteria: leads to a death, leads to a serious deterioration in the health of a subject that resulted in a life-threatening illness or injury, a permanent impairment of a body structure or a body function, in-patient hospitalization or prolongation of an existing hospitalization, medical or surgical intervention to prevent life-threatening illness or injury or permanent impairment to body structure or a body function, leads to fetal distress, fetal death or a congenital abnormality or birth defect. It is understood that planned hospitalization for a condition present prior to the subject's enrollment in the study cannot meet the definition of an SAE. An AE would meet the criterion of "hospitalization" if the event necessitated an admission to a health care facility (e.g., an overnight stay). Emergency room visits that do not result in admission to the hospital were evaluated for one of the other serious outcomes. For further reference, FIG. 12 summarizes classifications for the intensity or severity of each AE.

An adverse device effect (ADE) was considered an adverse event related to the use of catheter assembly (100), which included any adverse event resulting from insufficiencies or inadequacies in the instructions for use, the deployment, the implantation, the installation, the operation, or any malfunction of the investigational medical device; and any event that is a result of a use error or intentional abnormal use of the investigational medical device. A Serious Adverse Device Effects (SADE) was considered an adverse device effect that has resulted in any of the consequences characteristic of an SAE.

An unanticipated adverse device effect (UADE) or unanticipated serious adverse device effect (USADE) was considered any serious adverse effect on health, safety, any life-threatening problem, or death caused by, or associated with a device, if that effect, problem, or death was not previously identified in nature, severity, or degree of incidence in the investigational plan or risk analysis report, or any other unanticipated serious problem associated with a device that relates to rights, safety, or welfare of subjects. For all collected AEs, the AE's causality was determined with the degree of certainty about causality graded using the categories below as described in FIG. 12. The outcome of each AE was also assessed according to the classifications described in FIG. 13. FIGS. 14-15 refer to comprehensive list of foreseeable and anticipated adverse events. FIG. 16 shows a graphical overview of certain endpoints of the study and corresponding factors.

The purpose of this study was to assess the performance and safety of catheter configurations in as to accessibility into target areas of a beating heart, ease of manipulation, collection of electrode signals, and safety issues, including traumaticity to cardiac tissue and thrombogenicity. The primary objectives of this study were to assess the feasibility and safety for the use of the catheter of this for intracardiac mapping in the atria and ventricles. A secondary objective is to characterize the physician feedback of catheter assembly (100) regarding its deployment, use, and mapping results in the atria and ventricles. Feedback included a 7-point Likert-scale survey; that evaluated maneuverability and handling, pacing, unipolar and/or bipolar signal quality, workflow, visualization, and catheter interactions. This study demonstrated the feasibility and safety of using catheter assembly (100) in procedures for subjects in three different arrhythmia subgroups (VT, complex AT/re-do PAF, and persistent AF). Subjects were treated per investigator's standard of care and followed until 7 days post-procedure.

The catheter assembly of this disclosure was investigated for electrophysiological mapping of the heart with the herein disclosed navigation system. While prior catheters have played a role in this surge of higher density mapping, the study investigated the clinical benefits of catheter assembly (100) with its more than double the electrode number within a similar footprint. In particular, catheter assembly (100) was configured in the study to simultaneously collect multiple (e.g., up to 48 electrodes) intracardiac signals and facilitate faster mapping of cardiac arrhythmias using the herein disclosed navigation system.

A primary endpoint of the study was completion of pre-ablation mapping requirements and clinically indicated mapping with catheter assembly (100), without resort to non-study mapping catheter(s). The study also investigated the incidence of serious adverse events (SAE) during use of catheter assembly (100) and in comparison to non-study mapping catheter(s). Adverse events (AE) were understood as any untoward medical occurrence in a subject whether or not related to the investigational medical device.

Another endpoint of the study included investigating deployment, use, and mapping of catheter assembly (100) in the atria and ventricles based on physician feedback on post-procedure survey. Another endpoint of the study included investigating procedural characteristics, including but not limited to pre-ablation mapping time. In some examples, pre-ablation mapping time included pre-ablation mapping duration (e.g., FAM only and total time) by chamber and arrhythmia subgroup with the catheter. In some examples, pre-ablation mapping time included types and numbers of areas of interest captured with the catheter in pre-ablation mapping (e.g., PV triggers, previous PVI lesion gaps, ventricular scar slow conduction zone, critical isthmus for atypical flutter, focal and rotational activation patterns only for PsAF procedures). In some examples, pre-ablation mapping time included total procedure and mapping time.

Patient Selection

The criteria for patient selection, methods, personnel, facilities, and training specified in the first study were intended to minimize the risk to subjects undergoing this procedure. Subjects were prescreened carefully prior to enrollment in the study to ensure compliance with the inclusion and exclusion criteria. The exclusion criteria have been developed to exclude subjects with a medical history or condition that increases their risk of adverse events. Subjects must have had a pre-procedure Transesophageal Echocardiogram (TEE), Intracardiac Echocardiography (ICE), Magnetic Resonance Imaging Scan (MRI), or Computed Tomography (CT) scan to screen for the presence of thrombus, which is intended to decrease the potential for thromboembolic complications.

Inclusion criteria for the study included the following:
Diagnosed and is a candidate for clinically-indicated catheter ablation procedure for the management of ischemic ventricular tachycardia—OR—complex atrial tachycardia/atypical atrial flutter/paroxysmal atrial fibrillation following a pulmonary vein isolation ablation or mitral valve repair procedure, —OR—persistent atrial fibrillation;
Age 18 years or older;
Signed Patient Informed Consent Form (ICF); and
Able and willing to comply with all pre-, post-, and follow-up testing and requirements.
Exclusion criteria for the study included the following:
History of continuous AF sustained longer than 12 months;
History of AF<7 days and no previous AF ablation procedure;
Previously diagnosed with long-standing persistent atrial fibrillation;
Previously diagnosed with idiopathic PVC/VT;
Study arrhythmia secondary to reversible cause;
Atrial arrhythmias: patients with a left atrial size>55 mm;
LVEF≤25% for VT patients;
LVEF≤40% for AF patients;
Documented thrombus in the chamber to be mapped by the study catheter on imaging;
Contraindication to anticoagulation (e.g. heparin, warfarin, dabigatran);
History of blood clotting or bleeding abnormalities (e.g. hypercoagulable state);
Myocardial infarction within the past 2 months (60 days);
Documented thromboembolic event (including TIA) within the past 12 months (365 days);
Uncontrolled heart failure or NYHA function class III or IV;
Implanted with a pacemaker or intracardiac cardiac defibrillator within the past 3 months (90 days);
Implanted with a prosthetic valve;
Active systemic infection;
Diagnosed atrial or ventricular myxoma;
Implanted with an interatrial baffle or patch;
Atrial septal closure within the past 6 weeks (42 days);
Presence of a condition that precludes vascular access;
Presence of intramural thrombus, tumor or other abnormality that precludes catheter introduction or manipulation;
Women who are pregnant (as evidenced by pregnancy test if pre-menopausal); and
Enrollment in an investigational study evaluating another device or drug.

Further, any patient scheduled to undergo a clinically-indicated catheter ablation procedure for any of the following were screened, by the investigator or designated member for study eligibility, per the protocol inclusion and exclusion criteria:
1. Ischemic ventricular tachycardia (VT)
2. Complex atrial tachycardia/atypical atrial flutter/paroxysmal atrial fibrillation following a pulmonary vein isolation ablation or mitral valve repair procedure
3. Persistent Atrial Fibrillation (PsAF)

Pre-procedure assessments and data collection in the study were performed within 60 days prior to study procedure, including baseline Medical, Cardiac, and Arrhythmia History (including findings from TTM, ECG, Holter monitor, etc.); and transthoracic echocardiogram (TTE) imaging to assess left atrial size for atrial procedures and ejection fraction for all study procedures. In the day before or day of the study procedure, pre-procedure imaging was undertaken for detection of thrombus. Subjects meeting either of the following 2 criteria were required to have a pre-procedure TEE to screen for the presence of thrombus:
Has at least one risk factor for thrombus (such as structural heart disease, presence of risk factors for stroke (i.e., CHADS2 score>1), and atrial enlargement); and
Has been in atrial fibrillation for 48 hours or longer or for an unknown duration unless systemic anticoagulation at a therapeutic level has been maintained for at least three weeks Subjects who did not meet the above-referenced criteria could either have a TEE or one of the following methods used to screen for thrombus on the day before or the day of the study procedure, based on the patient's medical history and the investigator's medical judgment, including Computed Tomography (CT); Intracardiac Echocardiography (ICE); or Magnetic Resonance Imaging (MRI). Any time adverse events were observed after enrollment were collected and reported as appropriate.

Results of the First Study

In the study, 30 subjects were treated. A sample size of 30 subjects with a target of equal numbers of subjects (n=10) among the three study arrhythmia subgroups was determined to allow initial characterization of the performance and safety of catheter assembly (100). The sample size is also considered to provide sufficient data to initially characterize both the 15 mm and 20 mm spine lengths with primary use of the 15 mm length during the ventricular procedures, and primary use of the 20 mm length during the atrial procedures.

Standard descriptive summaries for continuous data include the number of observations with data, number of observations with missing data, mean, standard deviation, median, minimum, and maximum values. For categorical data, the count and percentage will be provided. Percentages will be based on the number of subjects without missing data.

Subjects were enrolled into the following three arrhythmia subgroups:
Ventricular Procedures:
1) Ischemic ventricular tachycardia (VT)
Atrial Procedures:
2) Scar-related atrial tachycardia (AT; includes atypical atrial flutter) procedures resulting from previous PAF ablation or mitral valve repair procedures or paroxysmal atrial fibrillation (PAF) "re-do" procedures
3) Persistent Atrial Fibrillation (PsAF)

The number of subjects who started the pre-ablation mapping procedures and the number of subjects who started the clinically indicated mapping with catheter assembly (100) summarized overall and by each arrhythmia subgroup. The number of subjects who completed the pre-ablation mapping requirements and the number of subjects who completed the clinically indicated mapping with catheter assembly (100) without resort to non-study mapping catheters were summarized overall and by each arrhythmia subgroup. The outcome was listed for the three arrhythmia subgroups. The number of subjects experiencing serious adverse events were summarized in the safety population overall and by each arrhythmia subgroup. The number of events were also reported. The SAEs were summarized by AE term, severity, causality, anticipation and outcomes overall and for each arrhythmia subgroup. AE data was also listed.

In the study, no evidence of thrombus was found during the in-life study with intracardiac echocardiography, on any of the catheters, or in any of the cardiac chambers in any of the three models sacrificed. Neither perforation was found nor significant trauma attributable to any of the catheters (except to the procedure-related transseptal punctures) was found in any of the hearts or their adjacent structures during gross necropsy. All hearts featured acute, minimal subendocardial hemorrhages in the chambers and mitral valves, but these hemorrhages were considered clinically insignificant due to their minimal extent.

It was also revealed that for patients with complex cardiac arrhythmias, catheter assembly (100) was clinically effective as a mechanism for eliminating or ameliorating persistent atrial fibrillation. The study also revealed that through the simultaneous and sequential collection of these intra-cardiac signals and the mapping procedure, catheter assembly (100) aided in the diagnosis of complex atrial and ventricular arrhythmias.

Intracardiac mapping of cardiac arrhythmias with the diagnostic catheter of this disclosure was significant for understanding and treating underlying issues that initiate and sustain them. In particular, catheter assembly (100) has more densely spaced electrodes and two of the configurations are larger than other prior catheters, including the catheter sold by Biosense Webster Inc., PENTARAY®. Catheter assembly (100) should possess the benefit of higher density mapping over a larger area, improving a physician's efficient identification of the areas of interest.

Overview of the Second Study

In a second study, mapping and/or treatment of PAF with the herein disclosed catheters was investigated, which is attached hereto in Appendix 3 and incorporated by reference in its entirety as if set forth verbatim herein. In particular, the performance of the second study investigated clinical safety and effectiveness of the catheter assembly of this disclosure to record and map a treatment site during the isolation of the atrial pulmonary veins in treatment of subjects with drug refractory, symptomatic, and paroxysmal atrial fibrillation. The study investigated EGM characteristics of the catheters in healthy right atria and utility for identifying conduction gaps through acutely created ablation lines. This prospective study included a six healthy swine (82.3±2.0 kg) studied under general anesthesia with isoflurane inhalation and mechanical ventilation. The research protocol was approved by the Institutional Animal Care and Use Committee and conformed to the Position of the American Heart Association on Research Animal Use. The study was performed at the Beth Israel Deaconess Medical Center Experimental Electrophysiology Laboratory in Boston, Mass.

In the study, the herein described catheter were investigated and included from five to eight arms (140), with the total number of electrodes ranging from 20 to 48. Each arm (140) included approximately six electrodes. The interelectrode spacing was approximately 2 mm edge-to-edge and 2.5 mm center-to-center for the catheters investigated with eight arms (140) whereas catheters with five arms (140) included variable interelectrode spacing alternating between 2 and 6 mm with the number of closely spaced bipoles increased from 10 to 24.

Ablation was performed in the study using a Thermocool Smart-Touch ST Surround Flow (ST-SF) catheter (Biosense Webster) at a power setting of 25 to 30 W for 20 seconds and in a point-by-point fashion. The target distance between applications was 3 to 4 mm and the target contact force was 10 to 20 grams. The aims of ablation were to characterize EGMs in ablated tissue and to evaluate the catheter with eight arms (140) in detecting gaps in comparison with the catheter with five arms (140). To do so, two vertical ablation lines were created at a posteroseptal and anteroseptal right atrium, avoiding the trabeculated tissue. The length of each line was estimated by measuring the center-to-center distances between the first and last ablation lesion tags. 1 to 2 ablation gaps were left in each animal to compare EGMs in this tissue between the catheters. The length of each gap was designed initially to be approximately 3 to 5 mm. This may have resulted from the expansion of the ablation lesion or due to catheter motion during ablation. For this reason, the distance between applications in intentional gaps was increased to 5 to 10 mm. The presence of gap was also verified by pacing (10 mA; 2 msec) with selective capture only at gap locations.

Immediately following ablation, the right atrium was remapped with both catheters during RAA pacing. The maps were created with special attention to the ablation line and with keeping a similar mapping density (number of points per line) between maps created with each catheter. After completion of the second mapping phase, triphenyl tetrazolium chloride (TTC) was infused 15 minutes before euthanasia, with the tissue additionally immersed in TTC to allow differentiation between metabolically active and inactive tissue. The endocardial dimensions of the line, line integrity, and gaps were documented. Color photographs were taken of the excised unfixed hearts, which were used for the diagnosis of linear continuity and/or gaps as the basis for evaluating the electroanatomical mapping findings.

Results of the Second Study

In the second study, mapping catheters of this disclosure with eight arms and 48 small and closely spaced electrodes were investigated in a swine model of acute atrial ablation lines. Its EGMs in the healthy atria were characterized and its utility for interrogating ablation lines with intentional gaps was evaluated in comparison to another five armed mapping catheter of this disclosure. As discussed more particularly below, the mapping catheter of this disclosure including eight arms (140) was observed to increases the mapping speed and density in comparison with the mapping catheter including five arms (140), which results from the higher number EGMs acquired at each beat. The EGM amplitude distribution in healthy atria was also observed as being lower with the mapping catheter of this disclosure including eight arms (140) compared with the mapping catheter of this disclosure including five arms (140).

The EGM amplitude distribution at sites of ablation gaps was also higher with the mapping catheter of this disclosure including eight arms (140) and is likely the result of its smaller sampling tissue size with an improved ability for identifying surviving myocardial tissue. Intact ablation lines were better characterized by the mapping catheter of this disclosure including eight arms (140) in comparison with the mapping catheter of this disclosure including five arms (140). EGM recorded with the mapping catheter of this disclosure including eight arms (140) were less susceptible to an annotation of far-field potentials and creation of false gaps. The mapping catheter of this disclosure including eight arms (140) was more accurate than the catheter of this disclosure including five arms (140) for identifying intact ablation lines reducing the frequency of false gaps due to far-field EGMs Descriptive statistics of the second study were reported as mean±SD and median for continuous parameters. In the study, it was found that the uniform electrode spacing of the catheter with eight arms (140) permitted recording overlapping EGMs, (e.g., 1-2, 2-3, 3-4, etc.) such that the overall number of bipolar EGMs recorded at each beat increased from 10 to 40. The coverage area of the catheter with eight arms (140) was similar to the catheter with five arms (140) as approximately 7.1 cm$^2$. The mapping density of the catheter with eight arms (140) was approximately 7 electrode/cm$^2$, which was significantly higher as compared to the catheter with five arms (140) at approximately 2.5 electrode/cm$^2$.

Electroanatomical mapping of the right atrium was also performed with the catheters of this disclosure during right atrial appendage (RAA) pacing at a rate slightly faster than the sinus (450-500 msec). To minimize the potential for a mapping bias, the order of mapping was alternated in the study such that in half the animals mapping was first performed with the catheter with eight arms (140) while in the other half mapping was first performed with the catheter with five arms (140). A map in the study was considered complete when the filling threshold reached 5 mm, such that interpolation between points was limited to approximately ≤5 mm. Data acquisition in the study was automated using the following inclusion criteria: (1) beat-to-beat timing stability of ≤5 msec (minimum of two consecutive beats); (2) distance from the premade anatomical shell of ≤3 mm. Collected data for each map included the following: (1) mapping time (defined as the time from the first to the last acquired beat); (2) number of points per map; and (3) mapping speed measured as the acquired number of points per minute of mapping. Data were additionally analyzed for EGM amplitude, duration, and ectopic burden. Atrial ectopy was assessed manually by counting all extra deflections on the RAA catheter tracing during active mapping. EGM analysis was performed offline at a sweep speed of 200 to 400 mm/sec on either the Carto 3 software (Biosense Webster) or LabSystem Pro EP recording system (Bard; Boston Scientific, Lowell, Mass.).

FIG. 17 is a table summarizing electrogram acquisition and performance measures in the healthy atria of the second study of this disclosure. As can be seen, mapping time was shorter with the catheter with eight arms (140) (3.2±0.79 minutes [median, 3.0] versus the catheter with five arms (140) which demonstrated a mapping time of approximately 6.9±2.67 [median, 7.0]). In addition, for the catheter with eight arms (140) the number of EGMs per map was significantly higher relative to the catheter with five arms (140) (2178±637 [median, 2103] versus 1046±238 [median, 1045]; P≤0.001). Consequently, the EGM acquisition rate was significantly faster with the catheter with eight arms (140) than the catheter with five arms (140) (665±193 points/min [median, 710] vs 160±56 points/min [median, 155]; P≤0.001).

Figure 18A:
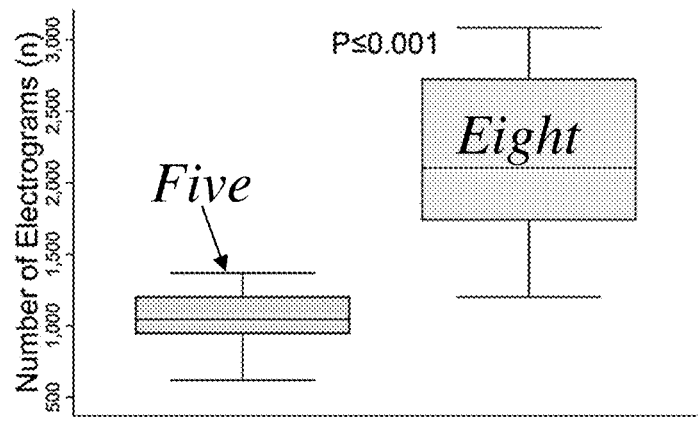
FIGS. 18A-18C depict graphical comparisons of electrogram acquisition parameters of the second study of this disclosure.
Figure 18B:
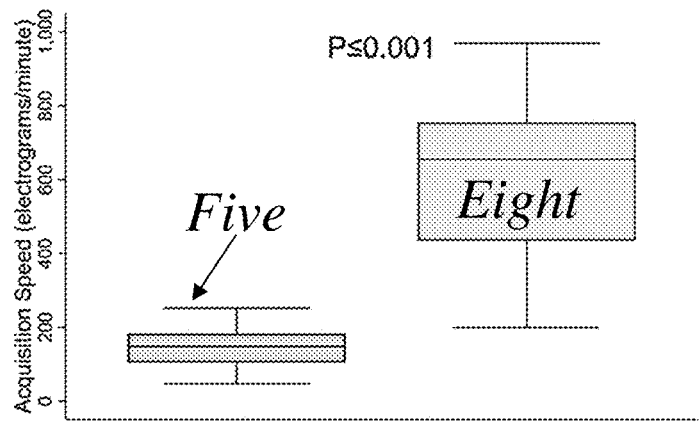
Figure 18C:
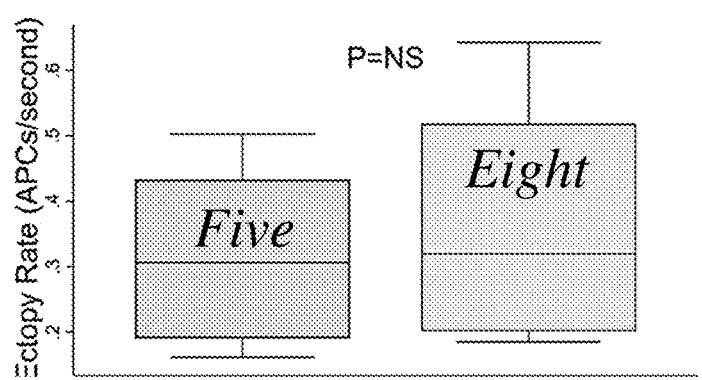

FIGS. 18A-18C compares the number of EGMs, acquisition rate and frequency of catheter-related ectopy between the catheters. As shown, the catheter with eight arms (140) collected a significantly higher number of electrograms per map (FIG. 18A) and at a significantly higher acquisition rate (FIG. 18B). The frequency of ectopy was similar between the catheters (FIG. 18C).

Figure 19A:
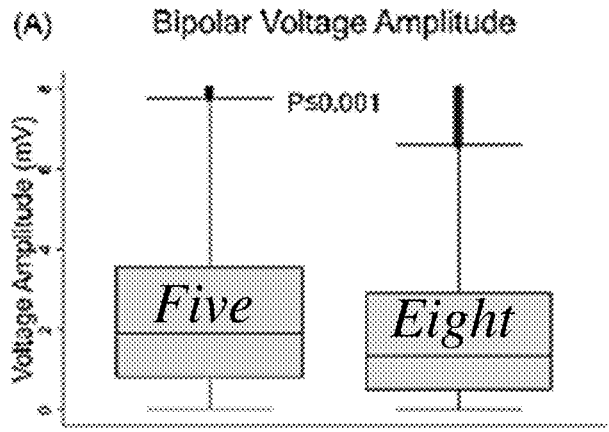
FIGS. 19A-19C depict graphical comparisons of electrogram characteristics of the second study of this disclosure.
Figure 19B:
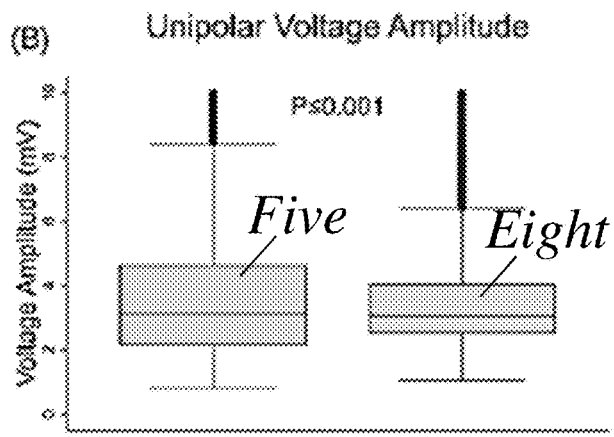
Figure 19C:
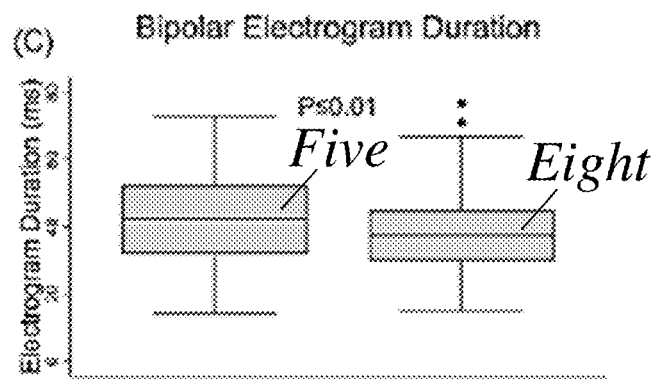

Comparison between catheter with five arms (140) and catheter with eight arms (140) electrogram characteristics in healthy atria. Specifically, electrograms recorded with the catheter with eight arms (14) exhibited lower bipolar (FIG. 19A) and unipolar (FIG. 19B) amplitudes. In addition, the electrogram duration (FIG. 19C) was shorter.

Figure 20A:
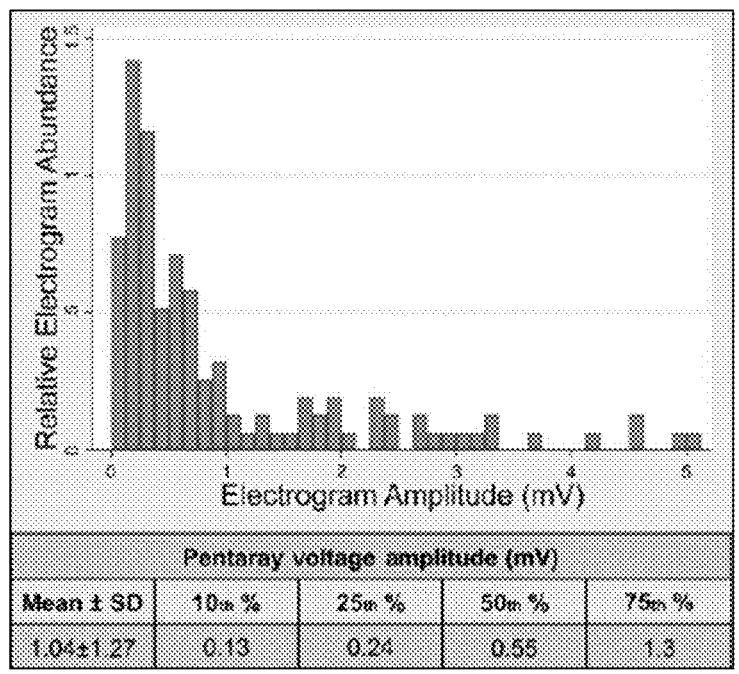
FIGS. 20A-20B show a graphical distribution of electrogram amplitude in ablation gaps.
Figure 20B:
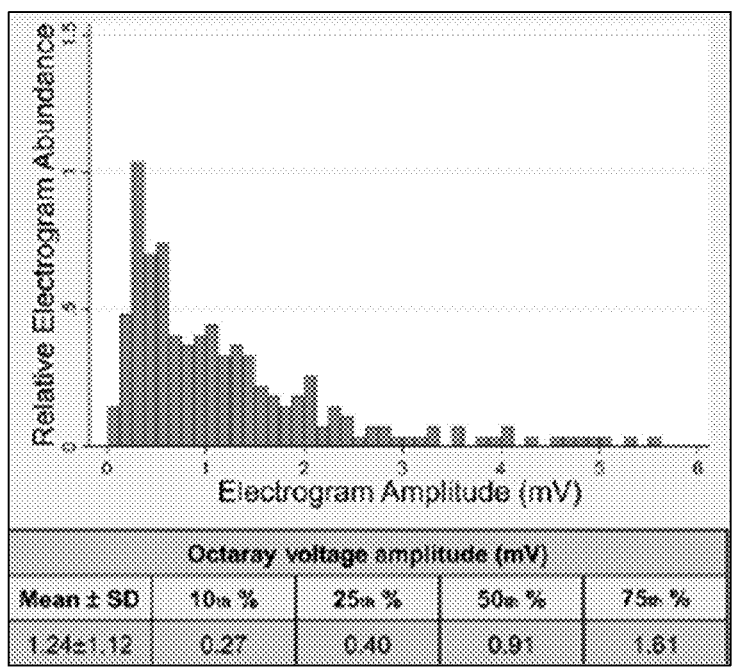

FIGS. 20A-20B show a histogram of EGM amplitude distribution in linear gaps for both the catheter of eight arms (140) and five arms (140). Electrograms recorded with the catheter of five arms (140) in areas of gaps were skewed toward lower values compared with electrograms recorded with the catheter of eight arms (140). The mean amplitude including quartiles was higher with the catheter of eight arms (140).

Figure 21C:
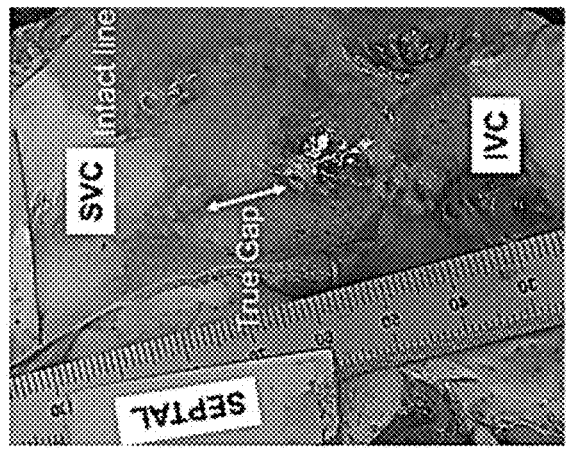
FIGS. 21A-21C show a single gap in the posteroseptal ablation line as identified by catheters investigated in the second study.
Figure 21B:
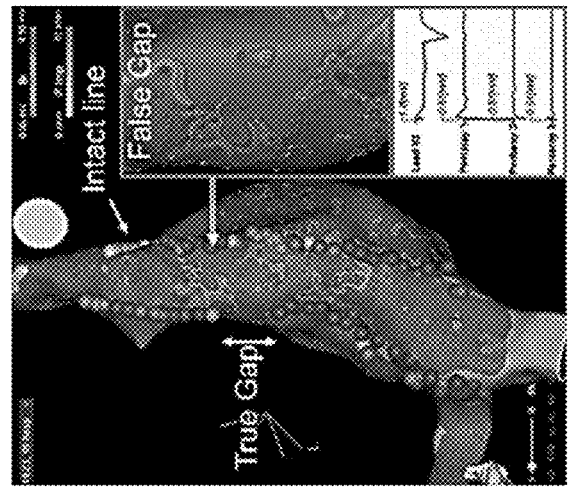
Figure 21A:
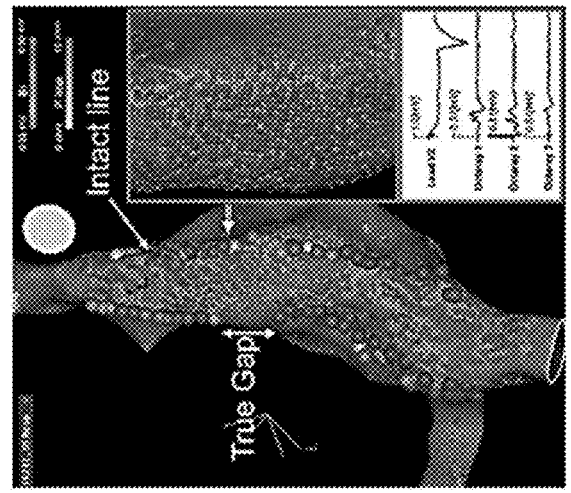

FIGS. 21A-C show a single gap in the posteroseptal ablation line as identified by both catheters (FIG. 21A for the catheter of eight arms (140) and FIG. 21B for the catheter of five arms (140)) investigated in the study and confirmed by pathology (FIG. 21C). As can be seen, comparison of gap identification by voltage mapping related to the catheter of eight arms (140) and of five arms (140). FIG. 21C shows the pathological findings of two ablation lines (animal #5). A single gap was identified in the posteroseptal ablation line (arrow) while the postero-lateral ablation line is intact.

Figure 22A:
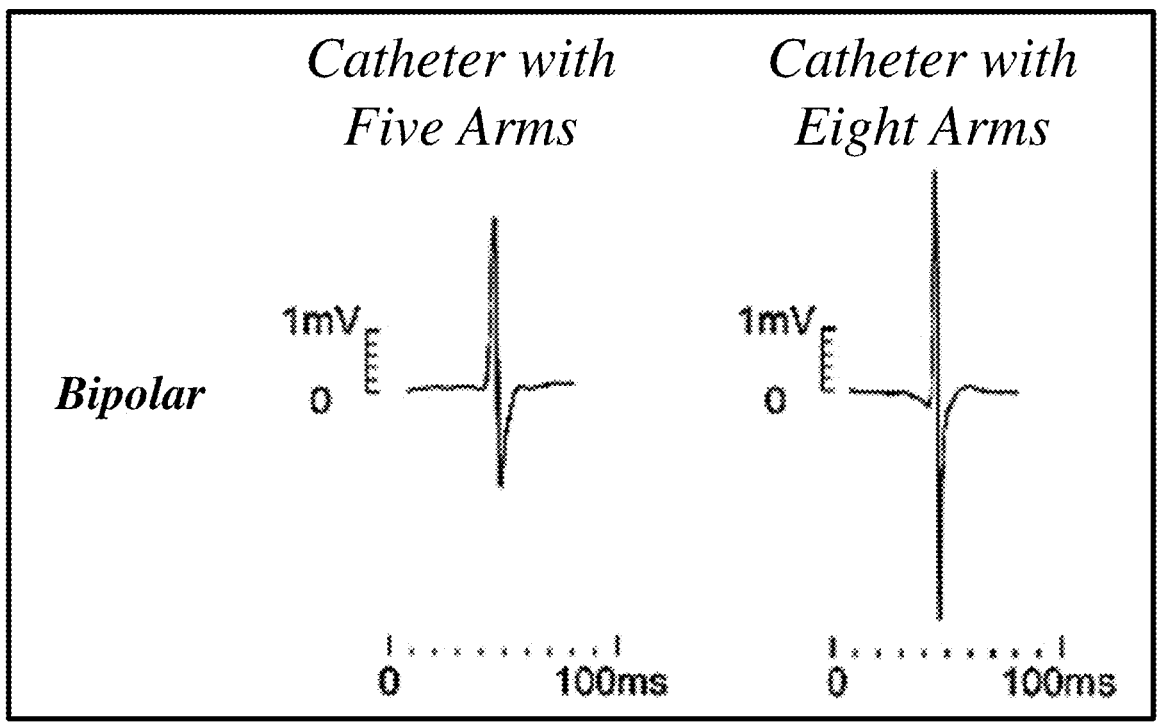
FIGS. 22A-B show representative examples of bipolar and unipolar electrograms sampled from approximately the same location in the right atrium with the electrogram amplitude scale.
Figure 22B:
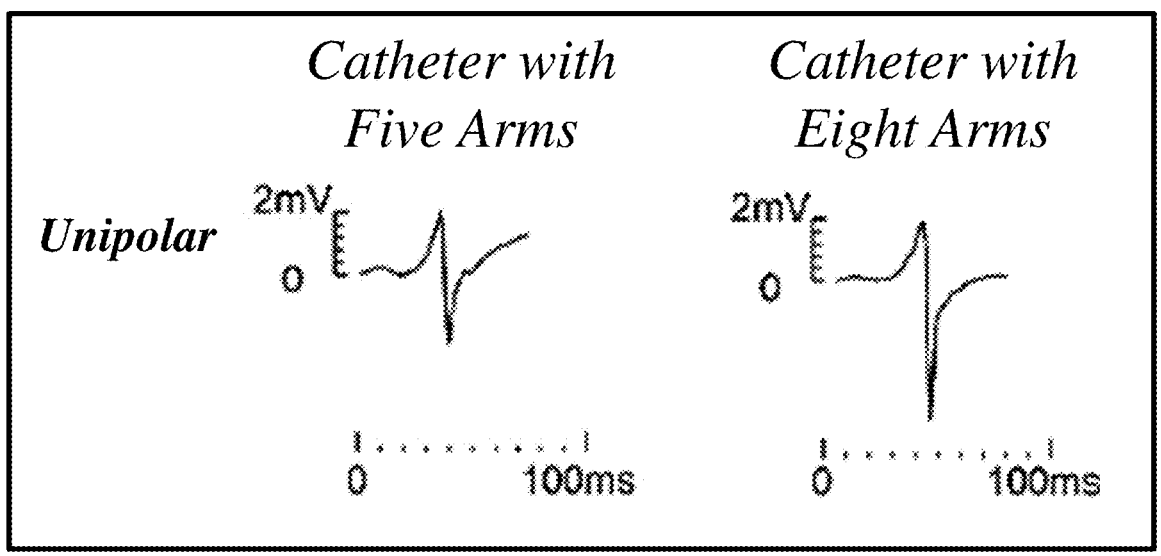

FIGS. 22A-B show representative examples of bipolar and unipolar electrograms sampled from approximately the same location in the right atrium with the electrogram amplitude scale. It can be seen between FIG. 17 to FIG. 22B that a total of 12,239 EGMs recorded with the catheter with eight arms (140) versus 5196 EGMs recorded with the catheter with five arms (140). It can be observed that the bipolar EGM duration was shorter with the catheter of eight arms (140) compared with the catheter of five arms (140) (38±12 ms [median, 38] vs 43±13 ms [median, 43]; P≤0.01). Overall, EGMs recorded with the catheter of eight arms (140) at healthy atria exhibited comparable voltage amplitude and shorter duration.

FIG. 22A and FIG. 22B show the voltage maps created with the catheter of eight arms (140) and of five arms (140), respectively. It was observed that the catheter of five arms (140) identified a "false gap" in the postero-lateral line. The insets show a detailed view of the area of interest (with ablation tags removed) and the EGMs recorded at the area of the false gap. EGMs recorded with the map generated by the catheter with eight arms (140) shows no local electrograms following the atrial pacing spike. In contrast, EGMs recorded with the catheter with five arms (140) show a far-field wide and multicomponent electrogram.

Figure 23A:
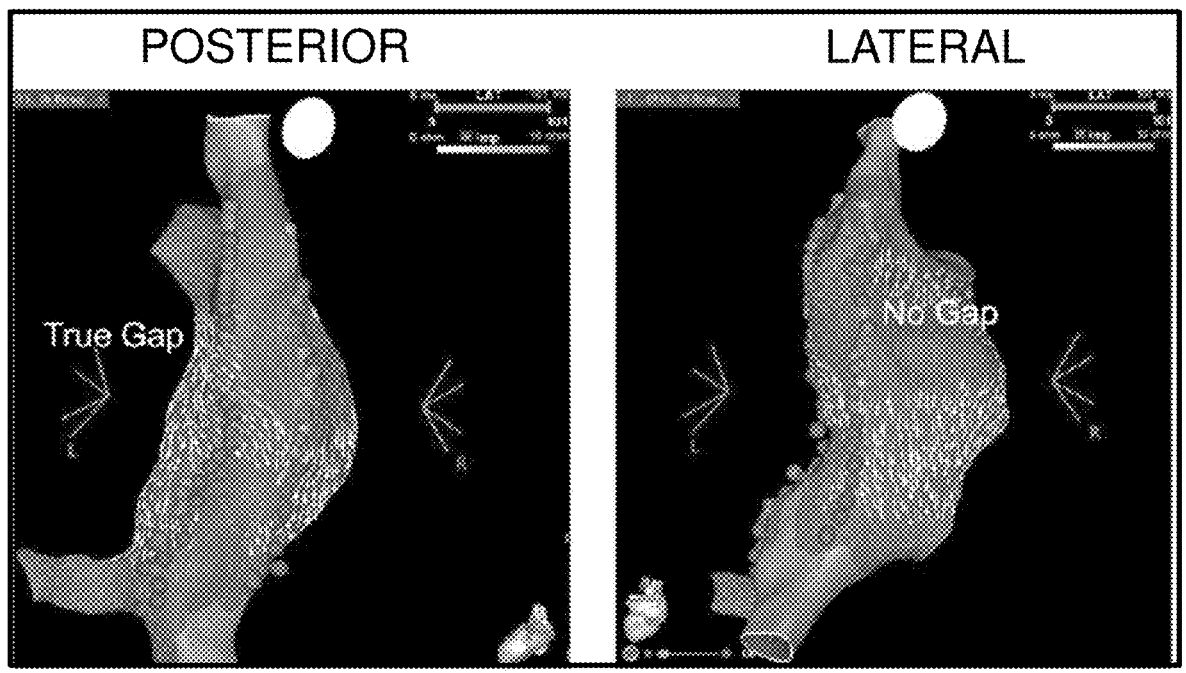
FIGS. 23A-B shows the corresponding activation map of FIGS. 22A-22B, respectively, with conduction through the gap.
Figure 23B:
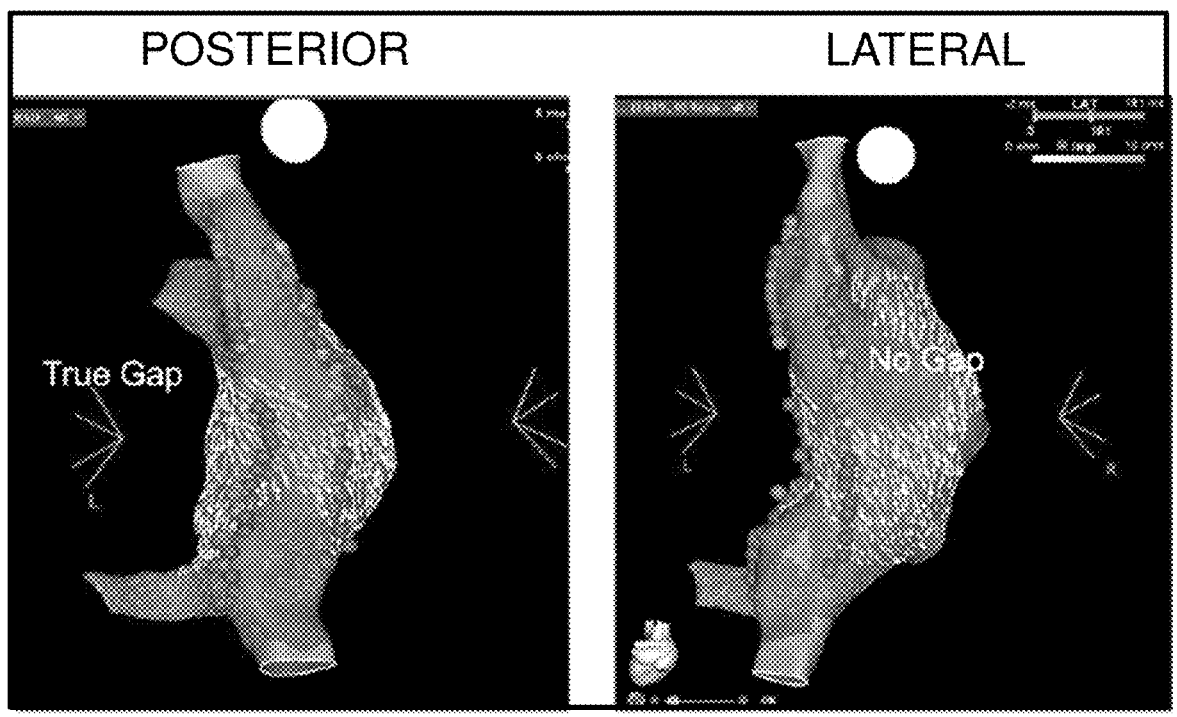
Figure 25A:
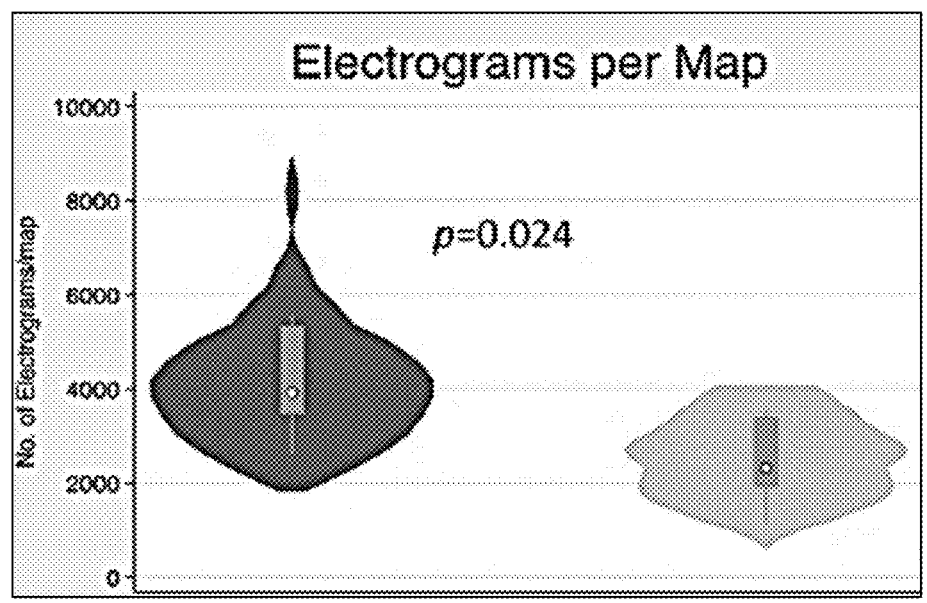
FIG. 25A shows a violin plot comparison of EGM acquisition data for each catheter of the third study as to EGMs per map.
Figure 25B:
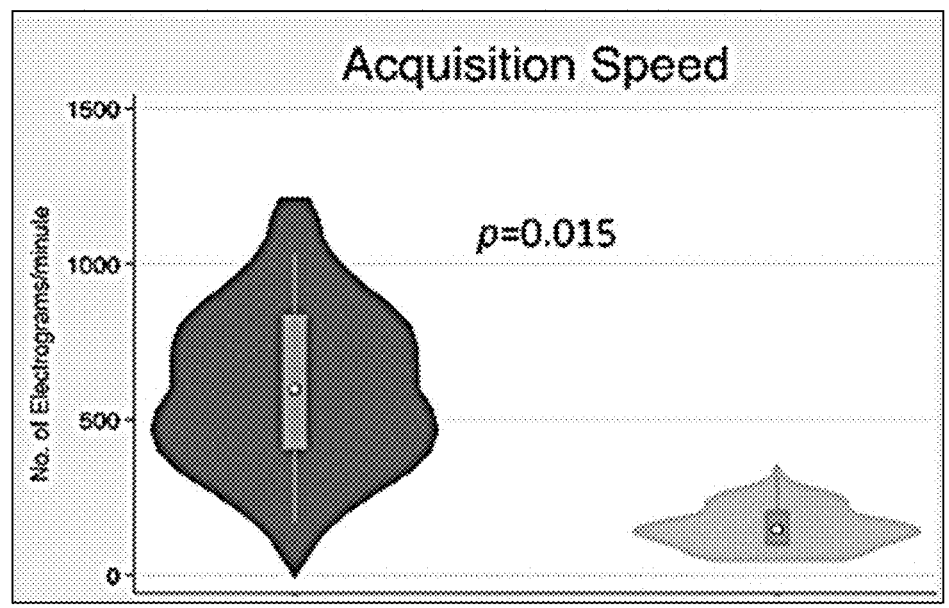
FIG. 25B shows a violin plot comparison of EGM acquisition data for each catheter of the third study as to acquisition speed.
Figure 26A:
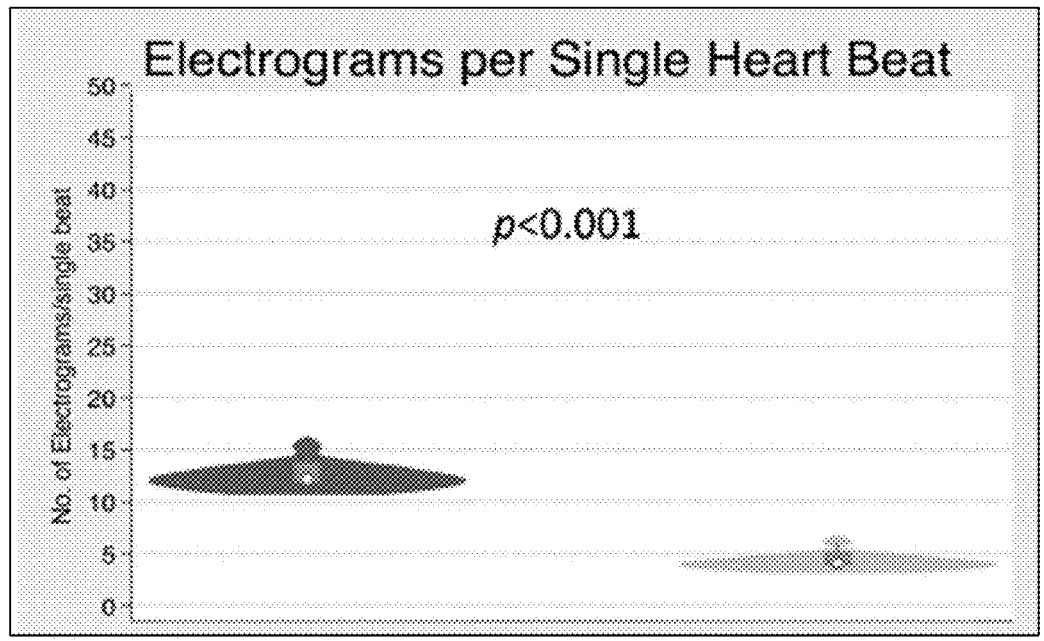
FIG. 26A shows a violin plot comparison of EGM acquisition data for each catheter of the third study as to EGMs per single heart beat.
Figure 26B:
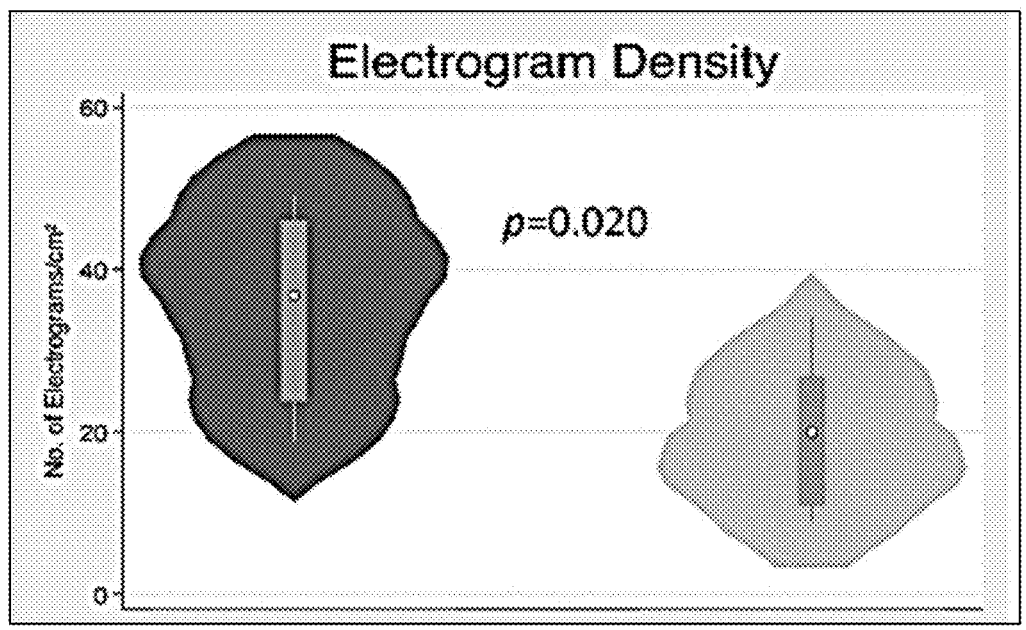
FIG. 26B shows a violin plot comparison of EGM acquisition data for each catheter of the third study as to electrogram density.

FIGS. 23A-B shows the corresponding activation map of FIGS. 22A-22B, respectively, with conduction through the gap. The postablation activation maps created with the catheter of eight arms (140) is shown in FIG. 23A and of five arms (140) in FIG. 23B depicting posterior and lateral projections. Note that during right atrial appendage pacing, there was conduction through the gap in the posteroseptal line. In comparison, there was no obvious conduction through the false gap in the postero-lateral line, although this is due to the parallel wavefront of propagation across the line The major difference between the catheters was surprisingly not related to either catheter's ability to identify macroscopic ablation gaps. Rather, the unexpected result related to the ability of the catheter of either arms (140) to accurately identify intact ablation lines. Pathology-proven intact lines were characterized by EGMs with bipolar voltage amplitude<0.5 mV recorded by both the catheter of eight arms (140) and of five arms (140). However, some areas of intact ablation lines exhibited higher bipolar voltage amplitude (≥1.0 mV) to falsely suggest the presence of a gap. The frequency of false gaps was higher with the catheter with five arms (140) (6 versus 2) and resulted from annotation of far-field EGMs. FIG. 21B in particular shows a representative example of the false gap as identified by the catheter with five arms (140).

Overview of the Third Study

In third second study, mapping and/or treatment of PAF with the herein disclosed catheters was investigated, which is attached hereto in Appendix 4 and incorporated by reference in its entirety as if set forth verbatim herein. In particular, the third study evaluated the catheters of this disclosure to record and map ventricles with heterogenous scar and to compare its utility to a standard multielectrode catheter. In the study, 12 swine were evaluated, including 4 healthy and 8 with healed infarction. As previously discussed, prior studies have shown good correlation between scar distribution in swine and humans with healed infarction. The LV was mapped with the catheter with eight arms (140) and compared with the catheter with five arms (140). Similar to the previously described studies, the catheter with eight arms (140) had more electrodes (e.g., 48 vs 20), each with a smaller surface area (0.9 mm$^2$ vs 2.0 mm$^2$) and spacing being fixed at 2 mm (versus 2-6-2 mm). EGM characteristics, mapping efficiency and scar description were compared between the catheters and cardiac magnetic resonance (CMR).

Anterior wall infarction was induced in 35-40 kg swine of either sex by balloon occlusion of the left anterior descending artery as previously described. A survival period of 10-12 weeks resulted in a large heterogeneous scar with surviving subendocardial bundles approximating infarction in humans. This infarction model often produces spontaneous and induced sustained reentrant monomorphic VTs. Following the survival period, animals underwent in-vivo cardiac magnetic resonance (CMR) imaging, followed by a terminal mapping procedure.

In-vivo cardiac magnetic resonance (CMR) imaging was performed in animals with healed infarctions≤1 week before the terminal mapping study. 3D late gadolinium enhancement (LGE) images were acquired 15-25 minutes after infusion of a bolus (2 mL/sec) of 0.2 mmol/kg Gadobenate Gimeglumine. A respiratory navigator placed on the dome of the right hemi-diaphragm was used for prospective real-time correction. A gradient echo sequence was imaged in short-axis plane covering the entire heart with the following typical parameters: TR/TE=2.7/1.3 ms; field of view=360× 324 mm2; flip angle=20°; spatial resolution=1.5×1.5×1.5 mm3; GRAPPA factor=2. Endocardial and epicardial contours were manually delineated in all slices and LGE was defined using a 6-SD thresh-old. Endocardial mesh was generated using a Poisson surface reconstruction from endocardial contours. LGE maps of the endocardium and sub-endocardium were defined by projecting LGE of endocardial region (2 mm inner layer) onto the mesh when all voxels along the region were defined as LGE positive.

Following a 6-8-week post-infarction survival period and ≤1 week after the CMR, animals underwent a terminal mapping procedure. An anatomical shell of the LV was built with either the catheters of this disclosure. Subsequently, an electroanatomical map of the LV was created with the catheters during RV septal pacing at a cycle length of 450-550 msec. To minimize the potential for a mapping bias, the order of mapping was alternated such that in half the animals mapping was first performed with the catheter including eight arms (140) while in the other half mapping was first performed with the catheter including five arms (140). A map was considered complete when the fill threshold had reached 5 mm for the entire surface area, such that interpolation between points was limited to ≤5 mm. The high pass filter was the same for the mapping catheters at 0.5 Hz for unipolar and 30 Hz for bipolar EGMs.

Data acquisition was automated using the following inclusion criteria: (1) QRS 180 morphology stability defined as ≥95% morphology stability compared to the paced QRS configuration; (2) activation time stability≤5 msec between 2 consecutive beats; and (3) maximal distance from the premade anatomical shell≤3 mm. Collected data included the following: (1) number of EGMs per map; (2) EGM acquisition rate, measured as the acquired number of points per minute of mapping; (3) EGM acquisition density, measured as the acquired number of EGMs per cm2 of LV, (4) number of EGMs acquired per beat, and (5) catheter-induced ectopy rate. The latter was measured by counting all unique ventricular activation events that were dyssynchronous with pacing (arose between pacing spikes) per minute of mapping. More sustained ventricular ectopy (e.g. a 3-beat catheter-induced run of VT) counted as a single ectopic event for the purposes of our analysis.

The minimum bipolar voltage amplitude of collected EGMs was 30 microvolts which is twice the noise level in our lab. All EGMs were manually reviewed to exclude ectopic beats and artifact. Activation time was annotated to the near-field potential. This was determined by presence of high-frequency potentials exhibiting spatiotemporal propagation across multiple electrodes at a similar acquired beat. EGMs were analyzed for amplitude, duration and morphology. The surface area of the infarction for each animal was defined by the outer circumference of abnormal EGMs: bipolar voltage amplitude approximately <1.5 mV and/or fractionated/split potentials as determined by the catheter including five arms (140).

Local abnormal ventricular activity (LAVAs) were defined as high-frequency potentials, possibly of low amplitude, distinct from a far-field ventricular electrogram occurring any-time during or after the far-field ventricular electrogram. Classification of EGMs was performed by two independent reviewers (MB and HY). In the case of discrepancy, EGM was reviewed by both reviewers. In the case of non-agreement, the EGM was not classified.

The catheter including eight arms (140) was also evaluated to record and map VT in regard to speed, EGMs quality and maneuverability. After completion of the maps during RV pacing, programmed stimulation was performed from the RV at a paced cycle length of 400-600 msec and with 1 to 5 extra stimuli down to ventricular effective refractory period. If pacing from the RV failed to induce sustained monomorphic VT, stimulation was repeated from the LV. In order to maximize the VT mapping time, the catheter including eight arms (140) was preemptively placed in the region of the infarct during stimulation. Non-tolerated VTs were defined as those resulting in mean arterial pressure<40 mmHg. These were terminated with pacing or cardioversion within 1 minute of non-tolerability.

Results of the Third Study

In the third study, EGM acquisition rate was faster with the catheter with eight arms (140)) as compared with the catheter with five arms (140) (814±126 vs 148±58 EGM/min, p=0.02). The faster, EGM acquisition rated resulted in higher density maps (38±10.3 vs 10.1±10.4 EGM/cm2, p=0.02). The catheter with eight arms (140) also recorded a higher proportion of near-field local abnormal ventricular activities than as compared with the catheter with five arms (140) (53±16% vs 34±16%, p=0.03). The catheter with eight arms (140) was generally observed as exhibiting increased mapping speed and ability to identify abnormal EGMs.

Mapping performance was compared separately for normal (n=4) and infarcted (n=8) ventricles. The number of EGMs acquired per beat was higher with catheter including eight arms (140) compared to the catheter including five arms (140) in both normal ventricles (12.8±1.1 vs 4.5±1.7 EGM/beat; p<0.001) and ventricles with healed infarction (10.6±2.1 vs 3.8±0.3 EGM/beat; p=0.001). EGM acquisition rate was faster with the catheter including eight arms (140) (normal: 814±126 vs 148±58 EGM/min p=0.015; infarct: 355±198 vs 174±84; p=0.005). The overall mapping time required to achieve a complete map was shorter with the catheter including eight arms (140) (normal: 5.3±0.9 vs 12.1±2.3 min, p=0.015; infarct: 14.8±7.5 vs 20.4±11.0 min, p=0.29). The number of EGMs per map was higher with the catheter including eight arms (140) (normal LV: 4202±962 vs 2255±898, p=0.024; infarcted LV: 4941±1915 vs 3297±1232; p=0.001). EGM density was also higher (normal LV: 38±10.3 v 20.9±10.4 EGM/cm2, p=0.02; infarcted LV: 29.1±11.3 vs 19.6±7.7 EGM/cm2; p=0.005). FIG. 24 is a table that summarizes difference in mapping performance between the catheters in healthy and infarcted myocardium. FIGS. 25A-26B show violin plots comparison of EGM acquisition data for each catheter of the third study. In particular, FIGS. 25A-26B depict graphical comparisons of electrogram acquisition performance with normal ventricles as to the catheter of eight arms (140) shown in the darker, violin on the left of each graph and the lighter, violin corresponding to the catheter of five arms (140). Data is shown in violin plots for visualizing the distribution of data. The darker box represents the 25-75$^{th}$ percentiles, the white dot represents the median and the extending line representing the 10-90$^{th}$ percentiles.

Figure 27B:
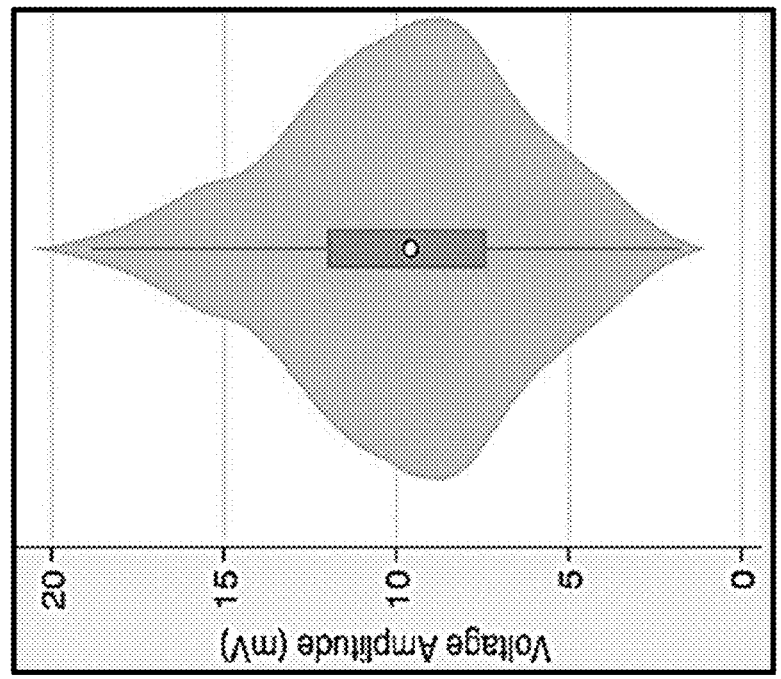
FIG. 27B describes unipolar voltage amplitude data of a catheter in the healthy left ventricle corresponding to the third study.
Figure 27A:
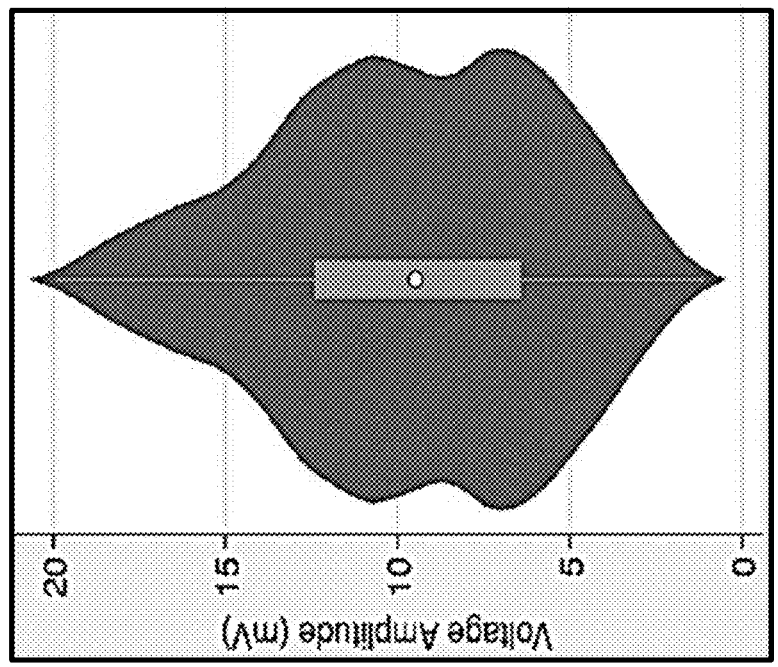
FIG. 27A describes unipolar voltage amplitude data of a catheter in the healthy left ventricle corresponding to the third study.
Figure 28B:
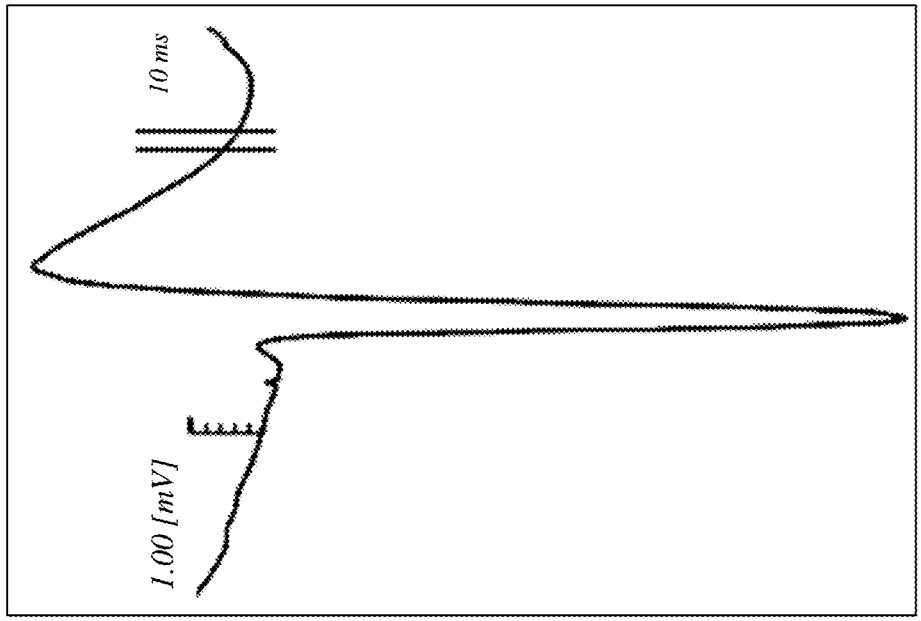
FIG. 28B describes unipolar voltage electrograms of a catheter in the healthy left ventricle corresponding to the third study.
Figure 28A:
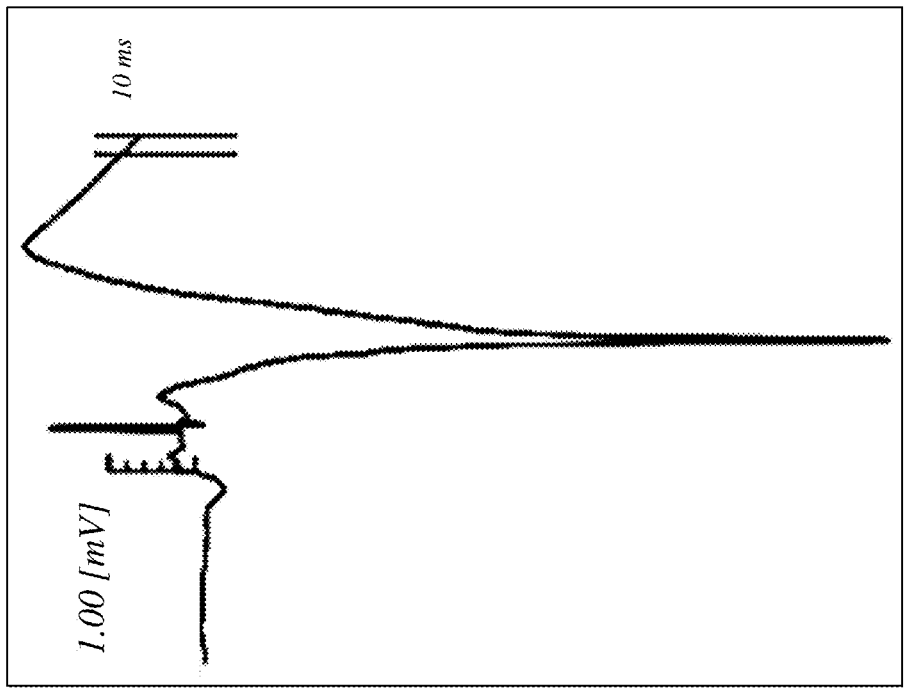
FIG. 28A describes unipolar voltage electrograms of a catheter in the healthy left ventricle corresponding to the third study.

FIGS. 27A-30B show comparisons of unipolar and bipolar voltage amplitude with EGM examples. Specifically, FIGS. 27A-27B describe unipolar voltage amplitude in the healthy left ventricle. Specifically, FIG. 27A represents data associated with the catheter including eight arms (140) whereas FIG. 27B represents the catheter with five arms (140). Representative electrograms are shown in the corresponding panels at similar gain and with scale at FIGS. 28A-28B, respectively. Note that electrogram duration recorded with the investigational catheter is shorter.

Figure 29B:
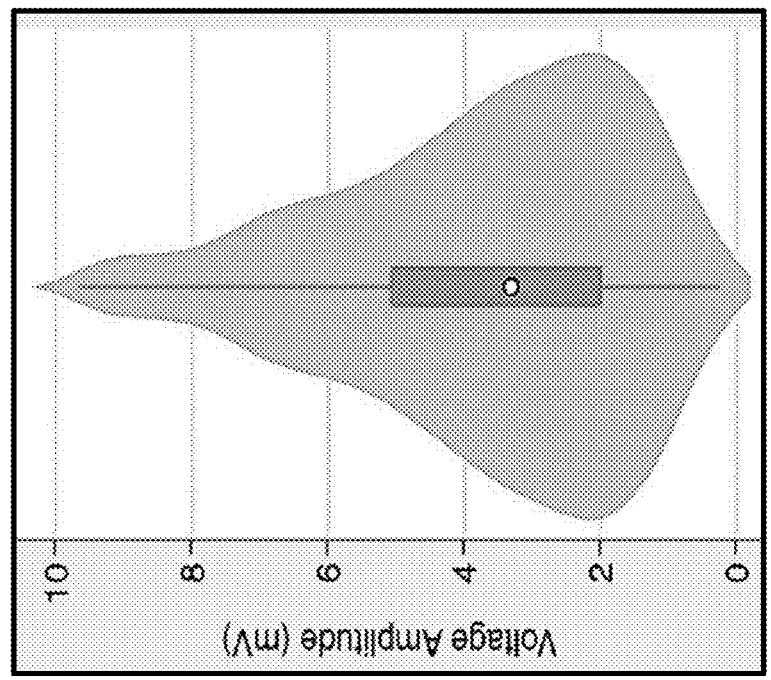
FIG. 29B describes unipolar voltage amplitude data of a catheter in the healthy left ventricle corresponding to the third study FIG. 30A describes bipolar voltage electrograms of a catheter in the healthy left ventricle corresponding to the third study.
Figure 29A:
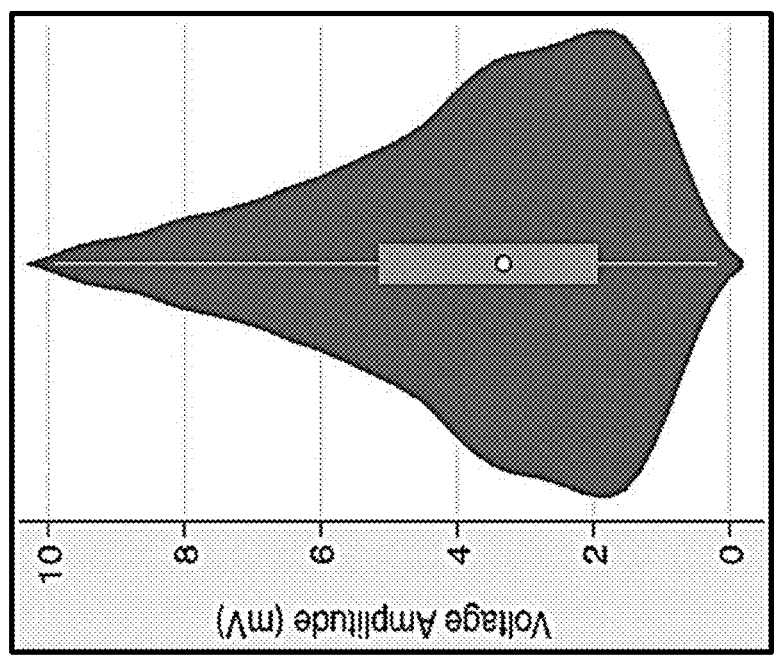
FIG. 29A describes unipolar voltage amplitude data of a catheter in the healthy left ventricle corresponding to the third study.
Figure 30A:
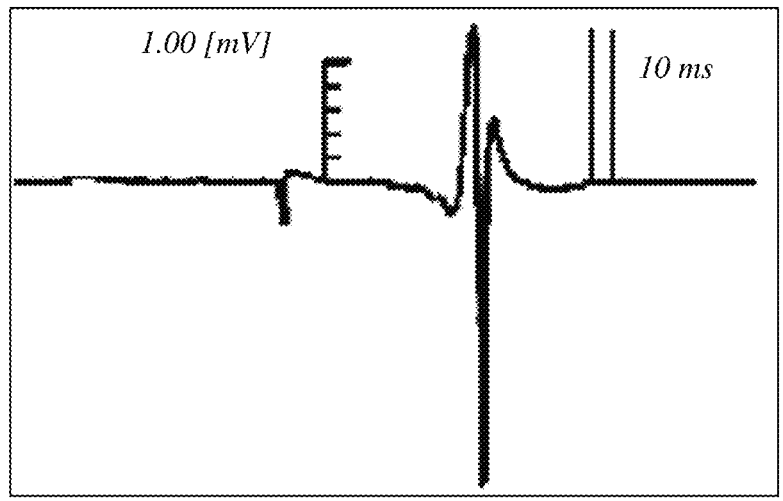
FIG. 30B describes bipolar voltage electrograms of a catheter in the healthy left ventricle corresponding to the third study.
Figure 30B:
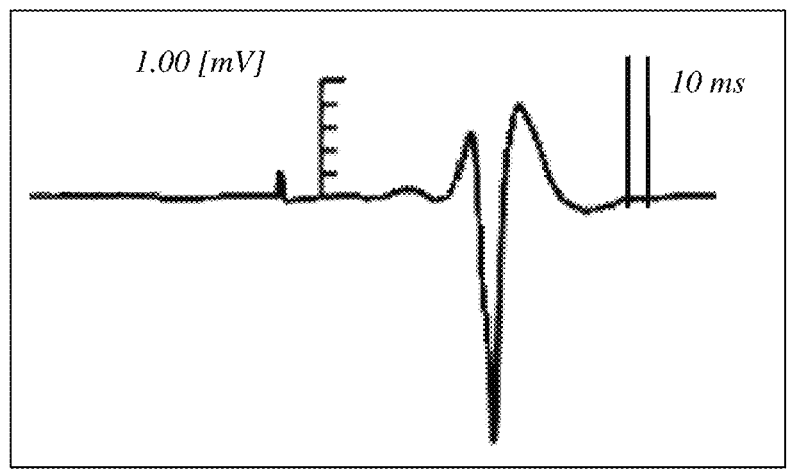

FIGS. 29A-29B describe bipolar voltage amplitude in the healthy left ventricle. Specifically, FIG. 29A represents data associated with the catheter including eight arms (140) whereas FIG. 29B represents the catheter with five arms (140). Representative electrograms are shown in the corresponding panels at similar gain and with scale at FIGS. 30A-30B, respectively. Note that electrogram duration recorded with the investigational catheter is shorter.

Figures 31A, 31B:
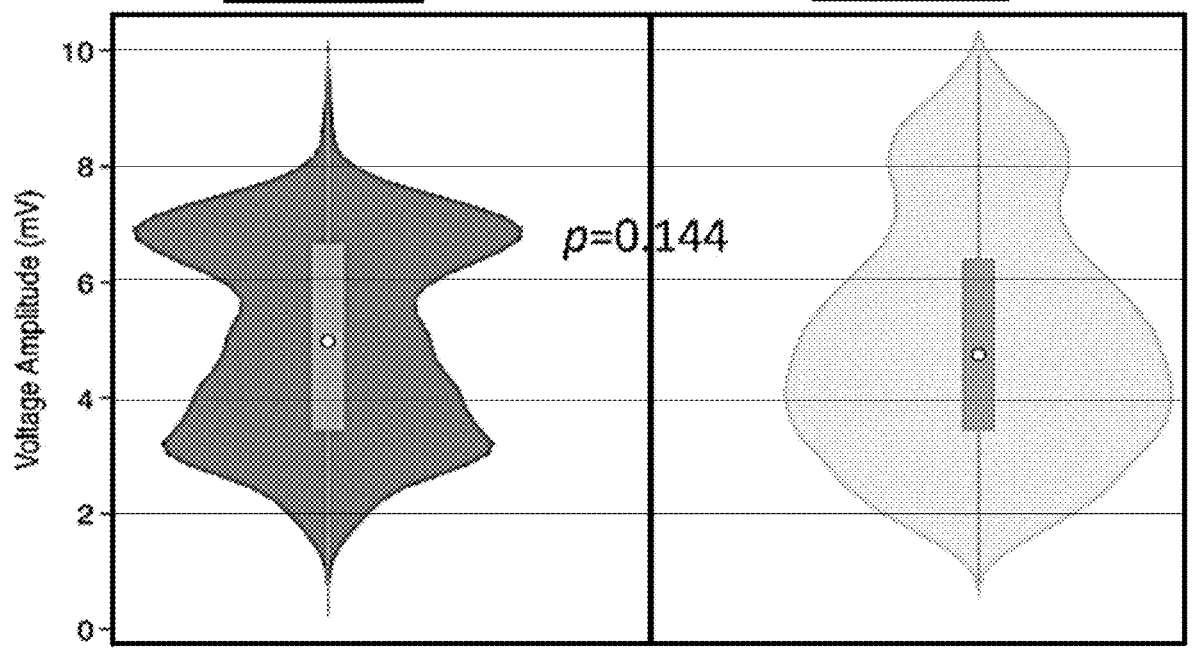
FIG. 31A depicts unipolar voltage amplitude distribution in violin plots in the left ventricular infarct region for a catheter of the third study of this disclosure.
FIG. 31B depicts unipolar voltage amplitude distribution in violin plots in the left ventricular infarct region for a catheter of the third study of this disclosure.
Figures 31C, 31D:
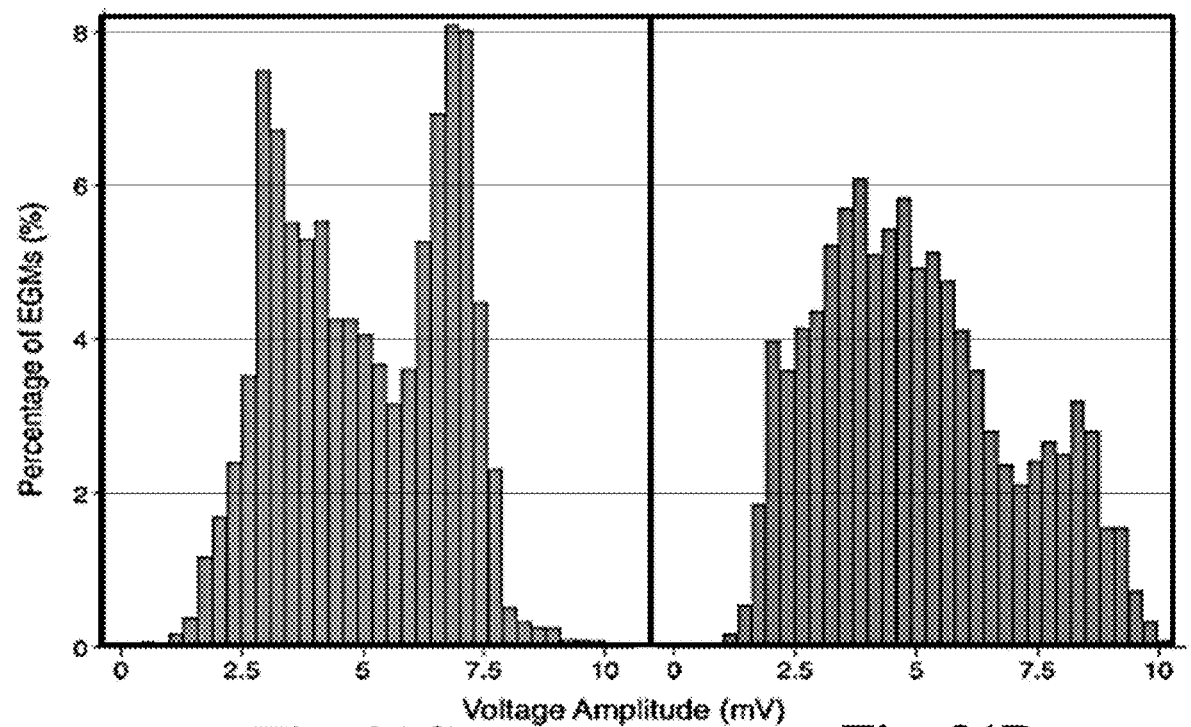
FIG. 31C depicts unipolar voltage amplitude distribution in histograms in the left ventricular infarct region for a catheter of the third study of this disclosure, whereby the histogram relates data shown in FIG. 31A.
FIG. 31D depicts unipolar voltage amplitude distribution in histograms in the left ventricular infarct region for a catheter of the third study of this disclosure, whereby the histogram relates data shown in FIG. 31B.

FIGS. 31A-32D show the unipolar and bipolar voltage distribution within the infarct with both catheters. Specifically, FIG. 31A depicts unipolar voltage amplitude distribution in violin plots in the left ventricular infarct region associated with the catheter including eight arms (140) whereas FIG. 31B depicts unipolar voltage amplitude distribution in violin plots in the left ventricular infarct region associated with the catheter including five arms (140). FIG. 31C depicts unipolar voltage amplitude distribution in histograms in the left ventricular infarct region for a catheter of the third study of this disclosure, whereby the histogram relates data shown in FIG. 31A. FIG. 31D depicts unipolar voltage amplitude distribution in histograms in the left ventricular infarct region for a catheter of the third study of this disclosure, whereby the histogram relates data shown in FIG. 31B.

Figures 32A, 32B:
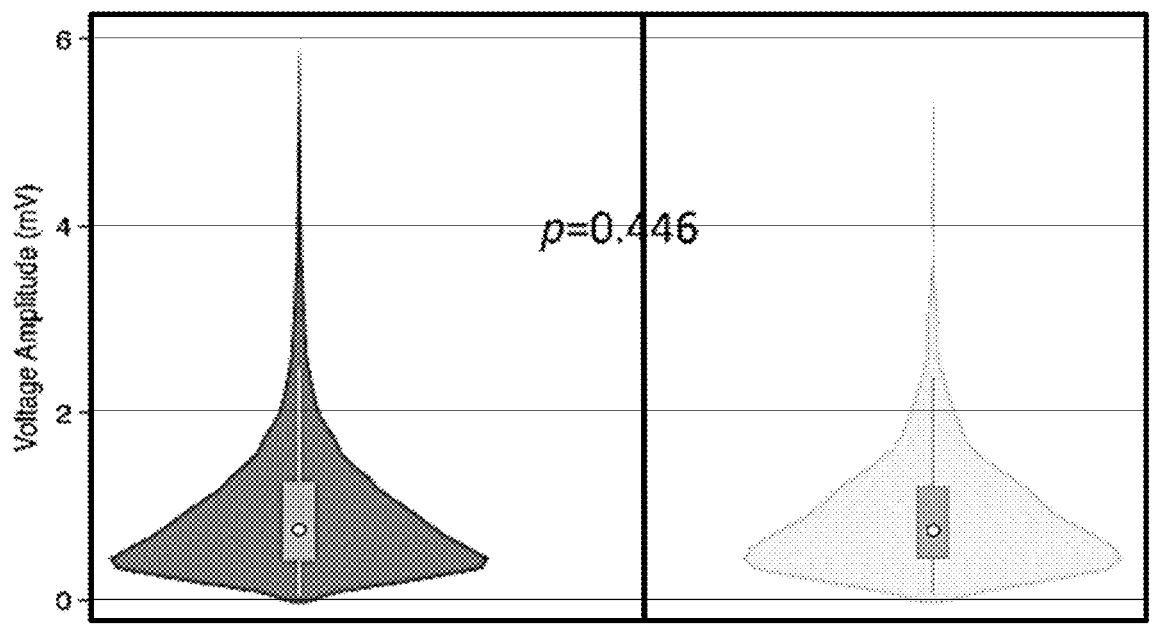
FIG. 32A depicts bipolar voltage amplitude distribution in violin plots in the left ventricular infarct region for a catheter of the third study of this disclosure.
FIG. 32B depicts bipolar voltage amplitude distribution in violin plots in the left ventricular infarct region for a catheter of the third study of this disclosure.
Figures 32C, 32D:
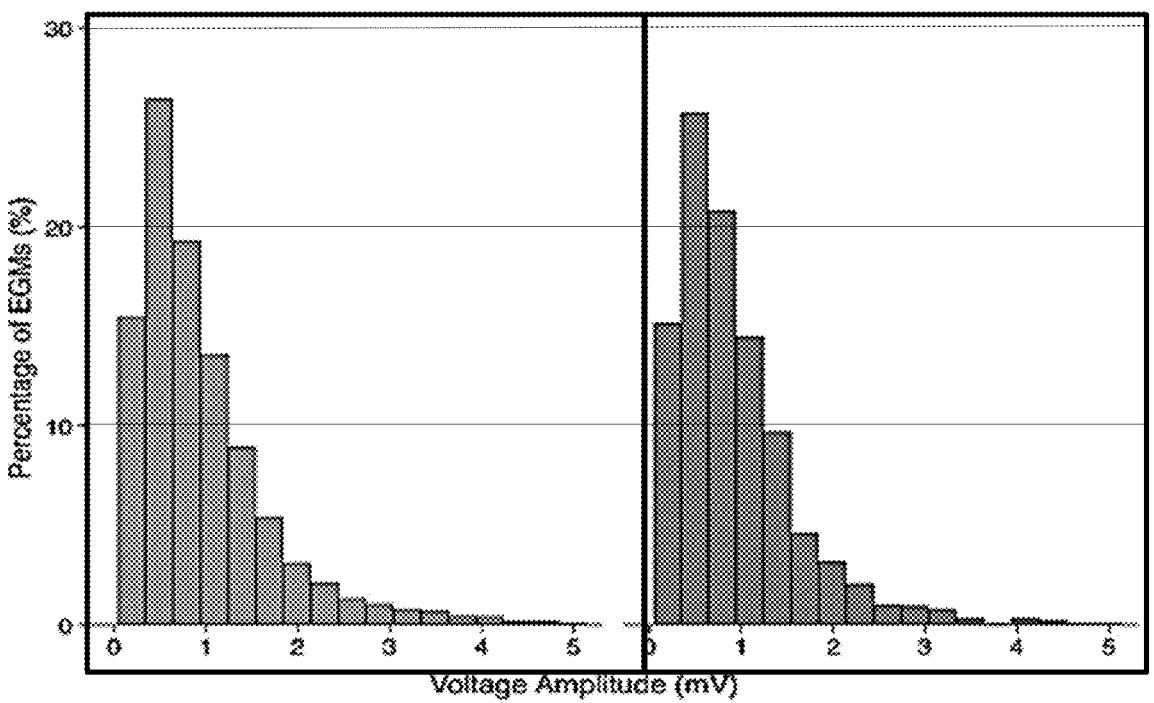
FIG. 32C depicts bipolar voltage amplitude distribution in histograms in the left ventricular infarct region for a catheter of the third study of this disclosure, whereby the histogram relates data shown in FIG. 32A.
FIG. 32D depicts bipolar voltage amplitude distribution in histograms in the left ventricular infarct region for a catheter of the third study of this disclosure, whereby the histogram relates data shown in FIG. 32B.

Similarly, FIG. 32A depicts bipolar voltage amplitude distribution in violin plots in the left ventricular infarct region for a catheter of the third study of this disclosure. FIG. 32B depicts bipolar voltage amplitude distribution in violin plots in the left ventricular infarct region for a catheter of the third study of this disclosure. FIG. 32C depicts bipolar voltage amplitude distribution in histograms in the left ventricular infarct region for a catheter of the third study of this disclosure, whereby the histogram relates data shown in FIG. 32A. FIG. 32D depicts bipolar voltage amplitude distribution in histograms in the left ventricular infarct region for a catheter of the third study of this disclosure, whereby the histogram relates data shown in FIG. 32B.

FIG. 33 a table summarizing the unipolar and bipolar EGM characteristics in the third study. A total of 13,676 and 6,268 EGMs were acquired in 4 normal LVs with the catheter including eight arms (140) and with five arms (140), respectively. Bipolar EGM duration was shorter with the catheter including eight arms (140) (33.1±11 msec 262 [median, 33] vs 39.6±12 msec [median, 40]; p<0.001. While voltage distribution within the infarct was similar between the catheters, the absolute and relative number of EGMs displaying LAVA was greater with the catheter including eight arms (140) (53±16 281% [2931/5428 scar EGMs] vs 34±16% [810/2382 scar EGMs], p=0.03).

Figure 34A:
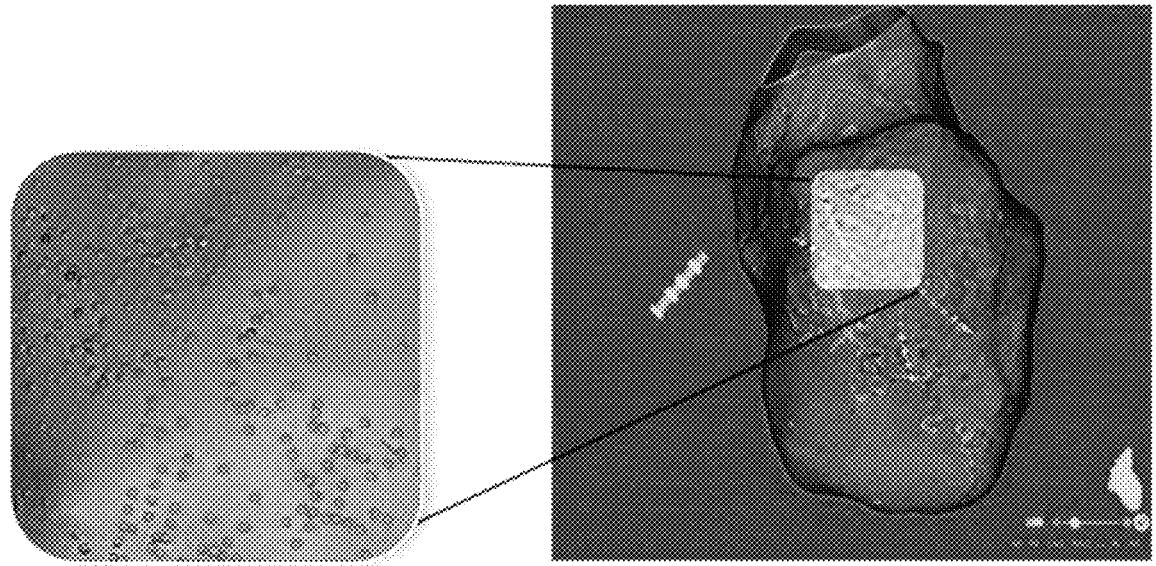
FIG. 34A depicts local voltage maps in the third study of a left ventricle with healed anterior wall infarction in a left anterior oblique view.
Figure 34B:
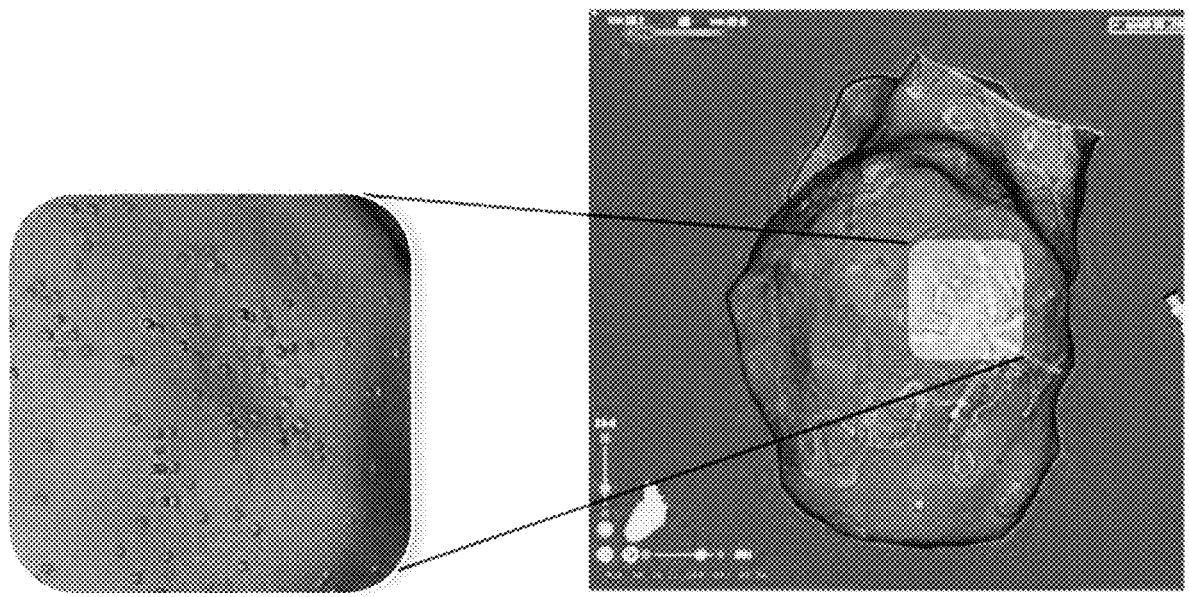
FIG. 34B depicts local voltage maps in the third study of a left ventricle with healed anterior wall infarction in a left anterior oblique view.

FIGS. 34A-34B depict local voltage maps of a left ventricle with healed anterior wall infarction in a left anterior oblique view. The bipolar voltage color scale ranges from 0.1 (lighter) to 1.5 mV 527 (darker). The highlighted rectangles show a higher magnification of a similar region recorded with the catheter including eight arms (FIG. 34A) and the catheter including five arms (FIG. 34B). Each dot in the higher magnification window represents a single electrogram. From each region, 16 representative electrograms are shown in the lower panels. Each electrogram (lighter tracing) is accompanies by a surface V1 ECG lead (darker tracing). Rectangles filled in represent electrograms with a high-frequency local abnormal ventricular electrogram (LAVA). It was observed that the larger proportion of LAVAs observed with the eight-armed catheter in comparison to the five-armed catheter.

A total of 17 sustained monomorphic Ventricular Tachycardias (VTs) were induced in 7 swine with healed myocardial infarction since in one swine, VT could not be induced. The number of VT configurations per heart was 2.1±1.7 (median, 1.5) and the CL was 261±15 msec. Of the 17 VTs, 13 (77%) were not hemodynamically stable and terminated by pacing or cardioversion. Twelve VTs were mapped (4 hemodynamically tolerated, 8 not tolerated). The mapping time of tolerated VTs was 18.2±6.4 306 min (median, 19.75 min) and the mapping time of the non-tolerated VTs was 0.9±0.3 min (median, 0.73 min). The EGM acquisition rate was similar between tolerated and non-tolerated VTs (29.2±12.3 EGM/beat [median, 35.6 EGM/beat] vs 21.0±10.4 EGM/beat [median, 21.3 EGM/beat]; p=0.456, respectively).

Figure 35C:
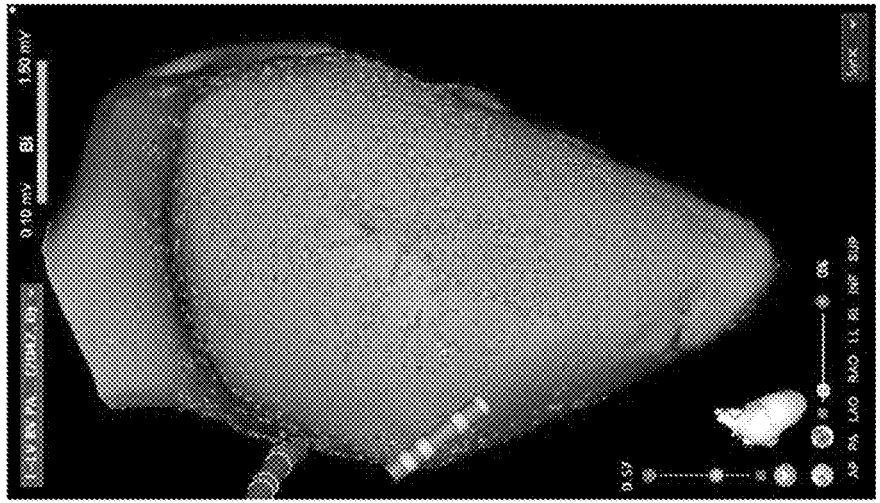
FIGS. 35A-35C depict examples of activation maps according to the third study with hemodynamically stable VT.
Figure 35B:
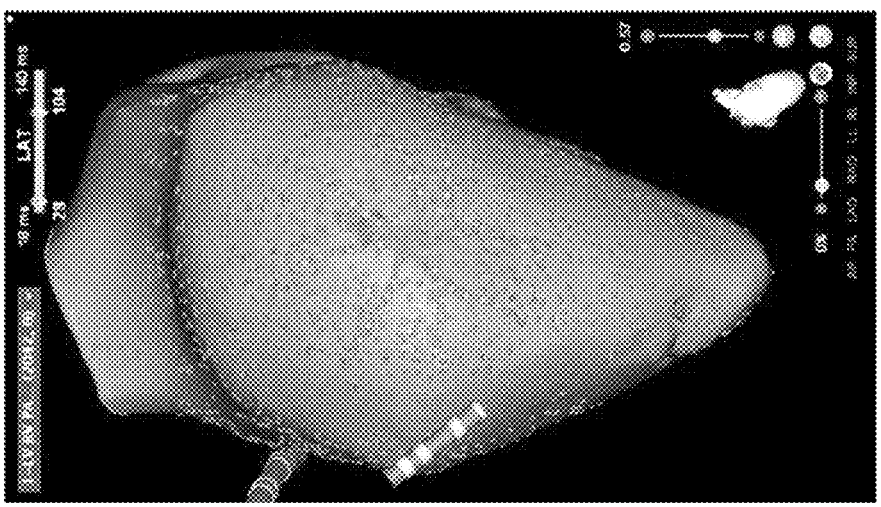
Figure 35A:
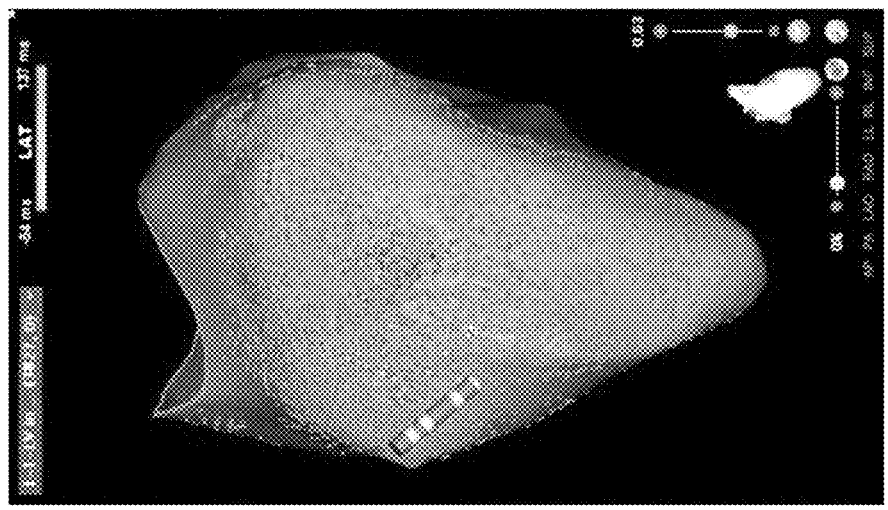

FIGS. 35A-35C depict representative examples of VT activation maps created in the third study with the catheter including eight arms (140). In particular, FIG. 35A shows an activation map of a stable VT with a mapping time of 21:31 min. A shadow of the catheter including eight arms (140) is shown over the isthmus with its corresponding diastolic electrograms. FIGS. 35B and 35C show the activation and voltage maps, respectively, during right ventricular (RV) pacing. In FIGS. 35A-35C, a cycle length was observed as approximately 265 msec, mapping time approximately 21:31 min, the number of EGMs being approximately 11,814, and approximately 15 EGMs/beat.

Figures 36A, 36B, 36C:
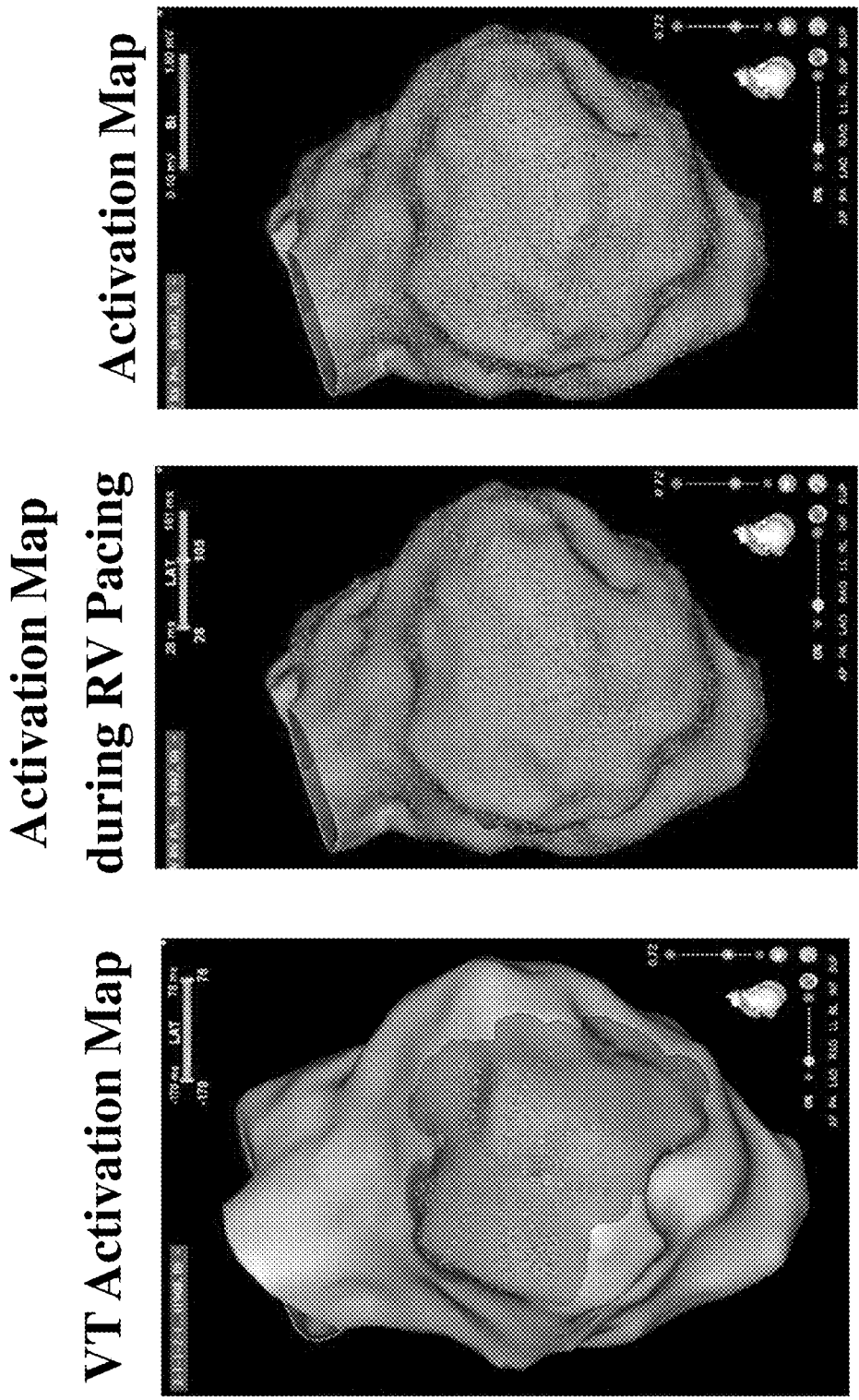
FIGS. 36A-36C depict examples of activation maps according to the third study with hemodynamically unstable VT.

FIGS. 36A-36C depict representative examples of VT activation maps created in the third study with the catheter including eight arms (140). In particular, FIG. 36A shows an activation map of an unstable VT. The examples of FIGS. 36A-36C depict an unstable VT that required early termination by cardioversion. A shadow of the catheter including eight arms (140) is shown over the isthmus with its corresponding diastolic electrograms. FIGS. 36B and 36C show the activation and voltage maps, respectively during right ventricular (RV) pacing. In FIGS. 36A-36C, a cycle length was observed as approximately 254 msec, mapping time approximately 18 sec, the number of EGMs being 1975, and approximately 37.1 EGMs/beat. Note, that even in an unstable VT shown in FIGS. 36A-36C, 18 seconds of mapping time with preemptive placement of the catheter in the area of interest before induction were sufficient to collect approximately 312 number of electrograms and to identify the diastolic pathway.

FIG. 37 depicts a method 3700 including 3710 placing a plurality of sensor electrodes in contact with tissue in a patient's cardiovascular system, the plurality of sensor electrodes being disposed on at least eight spines extending from a longitudinal axis; 3720 processing electrical signals from some of the plurality of sensor electrodes; 3730 plotting an electrocardiogram signal based on the processed electrical signals; and 3740 clinically improving pre-ablation mapping by maximizing contact and coverage of the catheter system within all four chambers of the heart.

FIG. 38 depicts a method 3800 including 3810 placing a catheter system to record and map electrical signals generated by cardiac tissues during treatment of atrial fibrillation in a group of patients, the system including an elongated body; a distal electrode assembly comprising a proximal stem, a plurality of spines emanating from the stem; and a plurality of nonconductive spine covers, each surrounding a respective spine, wherein each spine covers one or more tensile members of the respective spine cover; 3820 processing electrical signals from some of the plurality of sensor electrodes; 3830 plotting an electrocardiogram signal based on the processed electrical signals; and 3840 clinically improving pre-ablation mapping by maximizing contact and coverage of the catheter system within all four chambers of the heart.

FIG. 39 depicts a method 3900 including 3910 delivering a catheter system of this disclosure to one or more targeted pulmonary veins; and 3920 completing improving intracardiac mapping requirements and clinically indicated mapping with the catheter assembly, without resort to another one or more mapping catheters.

Figure 40:
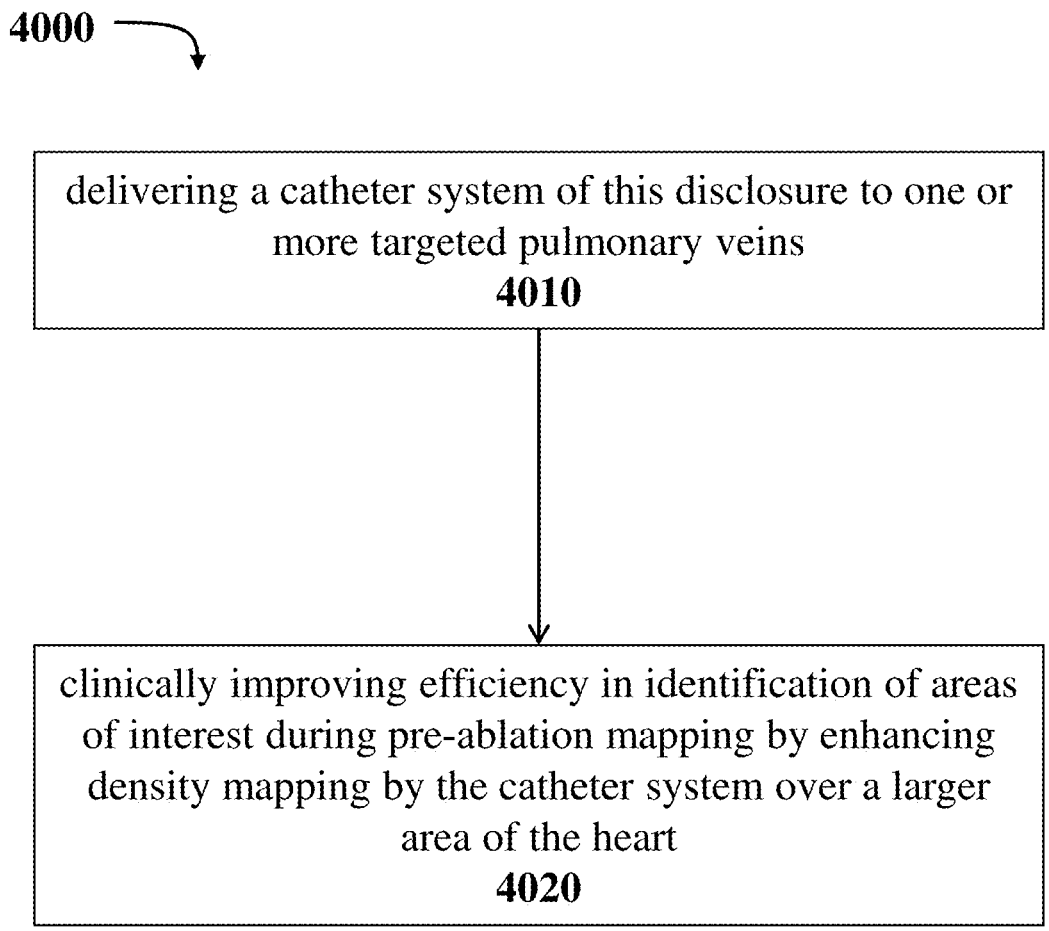
FIG. 40 depicts a graphical overview of one method according to this disclosure.

FIG. 40 depicts a method 4000 to record and map electrical signals in contact with tissue in a patient's cardiovascular system. The method 4000 can include 4010 delivering a catheter system of this disclosure to one or more targeted pulmonary veins; and 4020 clinically improving efficiency in identification of areas of interest during pre-ablation mapping by enhancing density mapping by the catheter system over a larger area of the heart.

FIG. 41 depicts a method 4100 to record and map electrical signals in contact with tissue in a patient's cardiovascular system. The method 4100 can include 4110 delivering a catheter system of this disclosure to one or more targeted pulmonary veins; and 4120 clinically improving diagnosis of complex atrial and ventricular arrhythmias through simultaneous and sequential collection intra-cardiac signals and the mapping the heart with the catheter system.

FIG. 42 depicts a method 4200 to record and map electrical signals in contact with tissue in a patient's cardiovascular system. The method 4200 can include 4210 delivering a catheter system of this disclosure to one or more targeted pulmonary veins; and 4220 clinically improving performance and safety of catheter configurations as to accessibility into target areas of a beating heart by mapping, by the catheter system, a treatment site of the one or more targeted pulmonary veins.

FIG. 43 depicts a method 4300 to record and map electrical signals in contact with tissue in a patient's cardiovascular system. The method 4300 can include 4310 delivering a catheter system of this disclosure to one or more targeted pulmonary veins; and 4320 clinically improving collection of electrode signals of the catheter system for pre-ablation mapping of a treatment site of the one or more targeted pulmonary veins.

Figure 44:
FIG. 44 depicts a graphical overview of one method according to this disclosure.

FIG. 44 depicts a method 4400 to record and map electrical signals in contact with tissue in a patient's cardiovascular system. The method 4400 can include 4410 delivering a catheter system of this disclosure to one or more targeted pulmonary veins; and 4420 clinically improving pre-ablation mapping safety, by the catheter system, as to catheter system traumaticity to cardiac tissue and thrombogenicity.

FIG. 45 depicts a method 4500 to record and map electrical signals in contact with tissue in a patient's cardiovascular system. The method 4500 can include 4510 delivering a catheter system of this disclosure to one or more targeted pulmonary veins; and 4520 clinically improving pre-ablation mapping by maximizing contact and coverage of the catheter system within all four chambers of the heart.

FIG. 46 depicts a method 4600 to record and map electrical signals in contact with tissue in a patient's cardiovascular system. The method 4600 can include 4610 placing a plurality of sensor electrodes of a catheter system in contact with tissue in a patient's cardiovascular system, the plurality of sensor electrodes being disposed on at least eight spines extending radially about a longitudinal axis, the catheter system including a mapping density of at least approximately 7 electrode/cm$^2$; 4620 processing electrical signals from some of the plurality of sensor electrodes; 4630 plotting an electrocardiogram signal based on the processed electrical signals; and 4640 improving mapping by maximizing contact and coverage of the catheter system within all four chambers of the heart.

The methods, systems, and devices of this disclosure demonstrated clinically effective and/or safe mapping catheter systems with for use with patients having certain conditions, such as PAF. The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method, comprising:
   placing a plurality of sensor electrodes of a catheter system in contact with tissue in a patient's cardiovascular system including a heart, the plurality of sensor electrodes being disposed on at least eight spines extending radially about a longitudinal axis and terminating in a free distal end;
   acquiring a plurality of electrograms (EGMs) from at least some of the plurality of sensor electrodes;
   generating a high density 3D local activation map for paroxysmal atrial fibrillation based at least in part on the plurality of electrograms;
   maximizing contact and coverage of the catheter system with cardiovascular tissue, by the plurality of sensor electrodes disposed on the at least eight spines extending radially about the longitudinal axis and terminating in the free distal end, within all four chambers of the heart; and
   identifying an intact ablation line having parallel wavefront propagation across the intact ablation line by using the high density 3D local activation map.

2. The method of claim 1, the plurality of sensor electrodes being part of the catheter system to record and map the plurality of EGMs during treatment of atrial fibrillation in a group of patients, the system comprising an elongated body; a distal electrode assembly comprising a proximal stem with the at least eight spines emanating from the stem; and a plurality of nonconductive spine covers, each surrounding a respective spine, each spine covering one or more tensile members of the respective spine cover.

3. The method of claim 2, further comprising: simultaneously collecting sensory information from up to 48 electrodes of the plurality of sensor electrodes of the distal electrode assembly, each spine comprising approximately six electrodes.

4. The method of claim 2, further comprising:
   increasing the amount of bipolar EGMs recorded at each beat by the catheter system from approximately 10 to approximately 40.

5. The method of claim 2, the catheter system comprising a mapping density of at least approximately 7 electrode/cm$^2$.

6. A method, comprising:
   placing a plurality of sensor electrodes of a catheter in contact with tissue in a patient's cardiovascular system;
   acquiring a plurality of electrograms (EGMs) from at least some of the plurality of sensor electrodes;
   generating a high density 3D local activation map for paroxysmal atrial fibrillation based at least in part on the plurality of electrograms (EGMs) with an average mapping time of approximately 3.2 minutes; and
   identifying an intact ablation line having parallel wavefront propagation across the intact ablation line by using the high density 3D local activation map.

7. The method of claim 6, the high density 3D local activation map being based at least in part on at least approximately 2000 electrograms.

8. The method of claim 6, the high density 3D local activation map being based at least in part on at least approximately 4000 electrograms.

9. The method of claim 6, the catheter system comprising an EGM acquisition rate of at least approximately 600 points/min.

10. The method of claim 6, further comprising:
    generating, by the catheter system, the high density 3D local activation map comprising at least approximately 38 EGM/cm$^2$.

11. The method of claim 1, further comprising:
    acquiring, by the catheter system, at least approximately 10 EGMs per beat.

12. The method of claim 2, further comprising:
    generating the high density 3D local activation map, by the catheter system, with an overall mapping time of approximately 5 minutes.

13. A method, comprising:
    placing a plurality of sensor electrodes of a catheter system in contact with tissue in a patient's cardiovascular system including a heart;
    increasing an amount of bipolar electrograms (EGMs) recorded at each beat by the catheter system from approximately 10 bipolar electrograms to approximately 40 bipolar electrograms;
    acquiring the bipolar electrograms from at least some of the plurality of sensor electrodes;
    generating a high density 3D local activation map for paroxysmal atrial fibrillation based at least in part on the bipolar electrograms;
    maximizing contact and coverage of the catheter system within all four chambers of the heart; and
    identifying an intact ablation line having parallel wavefront propagation across the intact ablation line by using the high density 3D local activation map.

* * * * *